(12) United States Patent
Otake et al.

(10) Patent No.: US 10,241,061 B2
(45) Date of Patent: Mar. 26, 2019

(54) NON-DESTRUCTIVE INSPECTION DEVICE AND METHOD

(71) Applicant: RIKEN, Wako-shi, Saitama (JP)

(72) Inventors: Yoshie Otake, Wako (JP); Yoshimasa Ikeda, Wako (JP)

(73) Assignee: RIKEN, Saitama (JP)

( * ) Notice: Subject to any disclaimer, the term of this patent is extended or adjusted under 35 U.S.C. 154(b) by 0 days.

(21) Appl. No.: 15/910,706

(22) Filed: Mar. 2, 2018

(65) Prior Publication Data

US 2018/0259462 A1 Sep. 13, 2018

(30) Foreign Application Priority Data

Sep. 9, 2015 (JP) .................. 2015-177762

(51) Int. Cl.
*G01T 3/06* (2006.01)
*G01V 5/00* (2006.01)
*G01N 23/204* (2006.01)

(52) U.S. Cl.
CPC ............. *G01N 23/204* (2013.01); *G01T 3/06* (2013.01); *G01V 5/0025* (2013.01)

(58) Field of Classification Search
CPC .................................................. G01N 23/204
See application file for complete search history.

(56) References Cited

U.S. PATENT DOCUMENTS

| | | | | | |
|---|---|---|---|---|---|
| 3,456,113 | A | * | 7/1969 | Keepin | G01N 23/09 |
| | | | | | 250/370.03 |
| 2015/0362618 | A1 | * | 12/2015 | Wraight | G01V 5/104 |
| | | | | | 250/269.8 |

FOREIGN PATENT DOCUMENTS

| | | | | | |
|---|---|---|---|---|---|
| JP | S60-250216 | A | * | 12/1985 | ............... G01V 5/00 |
| JP | 06-074920 | A | | 3/1994 | |
| JP | 10-185843 | A | | 7/1998 | |
| JP | 2005-227249 | A | | 8/2005 | |
| JP | 2008-180700 | A | | 8/2008 | |
| JP | 2008180700 | A | * | 8/2008 | .......... G01N 23/204 |
| JP | 2010-175362 | A | | 8/2010 | |
| JP | 2010175362 | A | * | 8/2010 | .......... G01N 23/204 |

OTHER PUBLICATIONS

Tayama et al., JP 2008-180700 A, Google Patents, English Translation, obtained Sep. 24, 2018 (Year: 2008).*
Hattori et al., JP 2010-175362 A, Google Patents, English Translation, obtained Sep. 24, 2018 (Year: 2010).*
International Search Report mailed in corresponding International Patent Application No. PCT/JP2016/076470 dated Nov. 29, 2016, consisting of 3 pp. (English Translation Provided).
Written Opinion mailed in corresponding International Patent Application No. PCT/JP2016/076470 dated Nov. 29, 2016, consisting of 4 pp.

* cited by examiner

*Primary Examiner* — David P Porta
*Assistant Examiner* — Jeremy S Valentiner
(74) *Attorney, Agent, or Firm* — Volpe and Koenig, P.C.

(57) ABSTRACT

A non-destructive inspection device 10 using backscattering of neutrons includes a neutron source 3 that radiates a pulse neutron beam to a surface 1a of an inspection target 1, a neutron detection device 5 that detects scattered neutrons scattered in the inspection target 1 and returned, and a measurement device 7 that measures the detection number of scattered and returned neutrons detected by the neutron detection device 5 and generates detection number data expressing the detection number with respect to time.

20 Claims, 21 Drawing Sheets

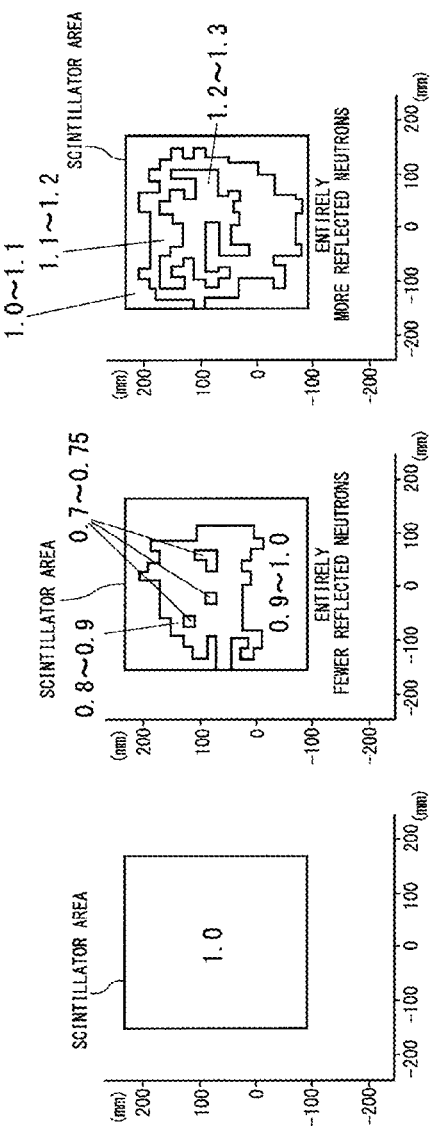

NON-DESTRUCTIVE INSPECTION DEVICE AND METHOD

CROSS REFERENCE TO RELATED APPLICATIONS

This application is a continuation-in-part of International Application Serial No. PCT/JP2016/076470, filed Sep. 8, 2016, which claims priority to Japanese Patent Application No. 2015-177762 filed on Sep. 9, 2015, which are all incorporated by reference as if fully set forth.

TECHNICAL FIELD

The present invention relates to a non-destructive inspection device and a non-destructive inspection method for making a pulse neutron beam incident on an inspection target, and inspecting presence or absence of a defect inside the inspection target, on the basis of neutrons returned from the inspection target.

BACKGROUND ART

A defect can occur in infrastructures such as a runway of an airport, a road (e.g., an express highway) for cars, a tunnel, and a bridge, due to the use thereof and deterioration with the elapse of time. For example, as the defect, a portion including water accumulated therein or a cavity can be generated inside the infrastructure.

For this reason, by inspecting the infrastructure, it is confirmed whether or not a defect has occurred in the infrastructure. As an inspection method, there is a method of measuring the properties of a road surface and inspecting whether or not the road surface is normal, on the basis of the measured values (see, e.g., PTL 1). For example, the road surface is scanned with a laser beam by using a laser scanner so that a crack ratio, rutting (a standard deviation of irregularities in a cross-sectional direction), and flatness (a standard deviation of irregularities in a longitudinal direction) is obtained, and on the basis of a function of them, a value is calculated. On the basis of the calculated value, it is determined whether or not the road surface is normal.

CITATION LIST

Patent Literatures

PTL 1: Japanese Patent Application Laid-open No. 2005-227249

PTL 2: Japanese Patent Application Laid-open No. 06-074920

SUMMARY OF INVENTION

Technical Problem

However, in the above-described inspection method, it is not possible to directly inspect presence or absence of a defect inside the road surface.

Meanwhile, it is also proposed that presence or absence of a defect inside an inspection target is inspected using neutrons. In this method, a neutron beam is made to be incident on the inspection target to detect neutrons having passed through the inspection target, a transmission image is generated on the basis of the detected neutrons, and a state (e.g., presence or absence of a defect) inside the inspection target is inspected on the basis of the image (see, e.g., PTL 2).

However, for a road surface and an inner wall of a tunnel, a transmission image of a neutron beam cannot be obtained. This is because a neutron detector cannot be disposed on a side (e.g., the inner side of the road surface) that is opposite to a side (e.g., the outer side of the road surface) on which the neutron beam is incident.

Consequently, an object of the present invention is to provide a non-destructive inspection device and a non-destructive inspection method that are capable of inspecting presence or absence of a defect inside an inspection target by using neutrons without disposing a neutron detector on a side (e.g., the inner side of a road surface) that is opposite to a side (e.g., the outer side of the road surface) on which a neutron beam is incident.

Solution to Problem

In order to accomplish the above-described object, according to the present invention, there is provided a non-destructive inspection device including a neutron source that radiates a pulse neutron beam to a surface of an inspection target;

a neutron detection device that detects scattered neutrons that are scattered in the inspection target and returned; and a measurement device that measures the detection number of the scattered neutrons detected by the neutron detection device, and generates detection number data expressing the detection number with respect to time.

The non-destructive inspection device can be configured, for example, as follows.

The detection number data is data in which each time point of the measurement is associated with the detection number at the time point of the measurement.

In this case, a time point at which the neutron source radiates the pulse neutron beam to the inspection target is a first time point, a time point that arrives by elapse of a set time from the first time point is a second time point, and the non-destructive inspection device preferably includes a calculation device that calculates an integrated value of the detection numbers at and after the second time point on the basis of the detection number data.

As another option, the detection number data may an integrated value of the detection numbers at and after a second time point that arrives by elapse of a set time from a first time point at which the neutron source radiates the pulse neutron beam to the inspection target.

The second time point is set such that among the scattered neutrons that are included in the pulse neutron beam radiated to the inspection target at the first time point, scattered in the inspection target, and returned, a predetermined proportion or more of the scattered neutrons that have energy greater than a set value occur during a period from the first time point to the second time point.

Thereby, most of the scattered neutrons detected at and after the second time point can be neutrons having low energy (in an example, thermal neutrons).

Neutrons easily react with water. Accordingly, when a portion containing water exists inside the inspection target, most of the scattered neutrons from this portion become low-energy neutrons. A time required for the low-energy neutrons to return is longer than that of high-energy neutrons. Accordingly, when the above-described integrated value is larger than a standard value, it can be determined that a defect portion containing water exists inside the inspection target. Here, the standard value is the above-described integrated value obtained in the condition that neither water nor a cavity (i.e., a void) exists inside the inspection target.

Meanwhile, when a portion of a cavity exists inside the inspection target, low-energy neutrons returned from the portion becomes small in the number thereof.

Accordingly, when the above-described integrated value is smaller than the standard value, it can be determined that a defect portion of a cavity exists inside the inspection target.

The second time point is set such that among the scattered neutrons that are included in the pulse neutron beam radiated to the inspection target at the first time point, scattered in the inspection target, and returned, a predetermined proportion or more of the scattered neutrons that have small energy equal to or less than a set value occur at and after the second time point.

The neutron detection device detects scattered neutrons for each position on an incident surface facing the surface of the inspection target, and the measurement device generates the detection number data for each position on the incident surface.

In order to accomplish the above-described object, according to the present invention, there is also provided a non-destructive inspection method including:

making a pulse neutron beam incident on a surface of an inspection target, and detecting scattered neutrons that are scattered in the inspection target and returned; and measuring the detection number of the scattered neutrons, and generating detection number data expressing the detection number with respect to time.

Advantageous Effects of Invention

According to the above-described invention, detection number data expresses, with respect to time, the detection number of scattered neutrons that are scattered in an inspection target and returned when a pulse neutron beam is made to be incident on the inspection target. The detection number data changes depending on presence or absence of a defect inside the inspection target. Accordingly, it is possible to determine presence or absence of a defect inside the inspection target, on the basis of the generated detection number data.

Thus, it is possible to determine presence or absence of a defect inside the inspection target without detecting neutrons having passed through the inspection target.

BRIEF DESCRIPTION OF DRAWINGS

FIGS. 8A to 8C illustrate data expressing integrated values of the numbers of reflected neutrons that are obtained in the cases of FIGS. 7A to 7C.

DESCRIPTION OF EMBODIMENTS

Figure 1:
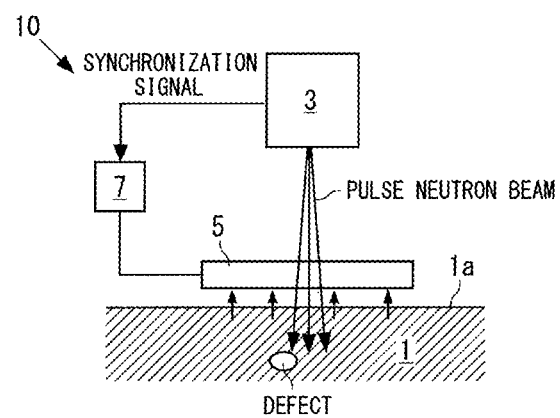
FIG. 1 illustrates a configuration of a non-destructive inspection device according to an embodiment of the present invention.

A preferred embodiment of the present invention is described with reference to the accompanying drawings. Meanwhile, common portions in the drawings are denoted by the same reference signs, and a repeated description is omitted.

FIG. 1 illustrates a configuration of a non-destructive inspection device 10 according to an embodiment of the present invention. The non-destructive inspection device 10 is a device for inspecting presence or absence of a defect inside an inspection target 1 by using backscattering of neutrons. The inspection target 1 may be an infrastructure such as a runway of an airport, a road (e.g., an express highway) of cars, a tunnel, and a bridge.

The non-destructive inspection device 10 includes a neutron source 3 that radiates a pulse neutron beam to a surface 1a of the inspection target 1 for minute duration, a neutron detection device 5 that detects scattered neutrons scattered in the inspection target 1 and returned, and a measurement device 7 that measures the number of scattered neutrons detected by the neutron detection device 5 and generates detection number data expressing the detection number with respect to time.

The duration of the pulse of the pulse neutron beam is preferably shorter than 0.1 milliseconds, but the duration is not limited thereto as long as the detection of a defect is not hindered. In addition, a synchronization signal indicating a time point of the radiation of the pulse neutron beam may be output to the measurement device 7 from the neutron source 3. On the basis of the synchronization signal, the measurement device 7 may generate detection number data at and after the time point of the radiation of the pulse neutron beam.

Figure 2A:
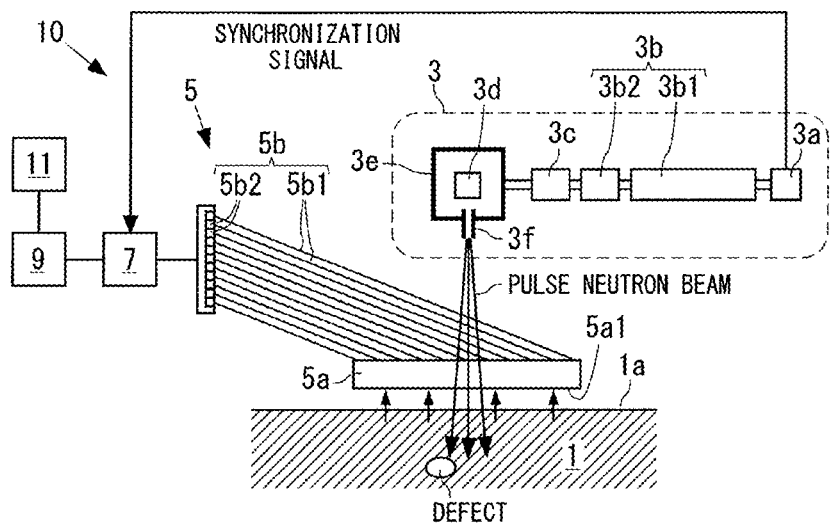
FIG. 2A illustrates a configuration example of the non-destructive inspection device according to the embodiment of the present invention.

FIG. 2A illustrates a configuration example of the non-destructive inspection device 10 according to the embodiment of the present invention. In FIG. 2A, the non-destructive inspection device 10 further includes a calculation device 9. Hereinafter, the non-destructive inspection device 10 is described in detail.

The neutron source 3 radiates a pulse neutron beam to the surface 1a of the inspection target 1, and makes the pulse neutron beam incident on the inspection target 1. In FIG. 2A, the neutron source 3 includes a charged particle source 3a, an acceleration device 3b, a beam adjuster 3c, a target 3d, a container 3e, and a tubular shielding member 3f.

The charged particle source 3a generates protons. The acceleration device 3b includes a plurality of accelerators 3b1 and 3b2 that sequentially accelerate protons generated by the charged particle source 3a. In a preferred example, the proton accelerated by the acceleration device 3b has energy equal to or greater than 1 MeV. The beam adjuster 3c includes a plurality of magnetic field coils that adjust a direction and a size of a proton beam accelerated by the acceleration device 3b, in accordance with the target 3d. The proton beam having passed through the beam adjuster 3c is incident on the target 3d. Thereby, neutrons are generated by reaction between the protons and the target 3d (e.g., beryllium). The target 3d is disposed within the container 3e that is formed of a material hardly transmitting neutrons. In the container 3e, a hole penetrating the container 3e from the outer surface thereof to the inside is formed. The tubular shielding member 3f for neutron radiation is attached to the hole. The tubular shielding member 3f is formed of a material hardly transmitting neutrons. Neutrons generated by the target 3d pass through the inside of the tubular shielding member 3f, thereby become a pulse neutron beam, and are incident on the inspection target 1. In this case, each of the neutrons of the pulse neutron beam has energy of, e.g., 0.1 to 5.0 MeV, but may be set to have an appropriate value in accordance with the type of inspection target 1.

The neutron detection device 5 detects scattered neutrons (hereinafter, referred to as reflected neutrons) that are included in the pulse neutron beam incident on the surface 1a of the inspection target 1 from the neutron source 3 and that are scattered on the surface 1a and inside the inspection target 1 and returned from the surface 1a.

Terms "scattering", "reflection", and "reflected neutrons" used below are defined as follows.

Scattering is a change in a moving direction of a pulse neutron beam (or particle). When seen from a substance (inspection target 1) on which the pulse neutron beam is incident, transmission corresponds to a direction in which the pulse neutron beam advances to (goes out to) a side opposite to the incident side of the pulse neutron beam, and reflection corresponds to a direction in which the pulse neutron beam advances to the incident side, and thus, transmission and reflection differ from each other in the advancement direction of the pulse neutron beam. In the present patent application, neutrons reflected as a result of scattering are used and detected.

Reflection means that an advancement direction of neutrons becomes opposite to an incident direction, as a result of one or a plurality of times of scattering. Accordingly, a reflection phenomenon basically accompanies a scattering phenomenon, and a specific case that is a result of the scattering phenomenon is equivalent to a reflection phenomenon. The details are as follows.

Scattering means that neutrons incident on the inspection target 1 from the neutron source 3 interact with the substance of the inspection target 1 to change an advancement direction and a speed thereof.

Reflection means that neutrons incident on the surface 1a of the inspection target 1 from the neutron source 3 are scattered in the inspection target 1 and returned from the surface 1a to the same side as the position of the neutrons before the incidence.

Reflected neutrons mean neutrons that are included in a pulse neutron beam (i.e., a large number of neutrons constituting the pulse neutron beam) and that are incident on the inspection target 1 from the neutron source 3 and returned to the same side as the position of the pulse neutron beam before the incidence from the surface 1a by scattering (backscattering) in the inspection target 1.

Another part of the pulse neutron beam incident on the inspection target 1 from the neutron source 3 is absorbed by interaction with the inspection target 1 (i.e., changed into heat or another radiation), and disappears.

In addition, still another part of the pulse neutron beam incident on the inspection target 1 from the neutron source 3 may pass through the inspection target 1 without being absorbed in the inspection target 1, and advances to the outside of the inspection target 1 from a surface (not illustrated) of the inspection target 1 on a side opposite to the surface 1a.

Accordingly, the following relation expression is established among the number $N_I$ of neutrons incident on the inspection target 1 from the neutron source 3, the number $N_R$ of reflected neutrons, the number $N_A$ of neutrons absorbed into the inspection target 1 by interaction with the inspection target 1, and the number $N_P$ of neutrons having passed through the inspection target 1.

$$N_I = N_R + N_A + N_P$$

However, for convenience of description, it is assumed here that neutrons advancing in the inspection target 1 in a direction parallel to the surface 1a are absorbed in the inspection target 1. In other words, it is assumed that the inspection target 1 infinitely extends in a direction parallel to the surface 1a.

In FIG. 2A, the neutron detection device 5 includes a neutron detector 5a that is a scintillator, and a photo detector 5b.

The scintillator 5a is provided at a position facing the surface 1a of the inspection target 1 on which a pulse neutron beam radiated from the neutron source 3 is incident.

The scintillator 5*a* includes an incident surface 5*a*1 on which neutrons reflected from the surface 1*a* are incident, and emits light by the incident reflected neutrons.

The photo detector 5*b* detects the light emitted by reflected neutrons incident on each position on the incident surface 5*a*1.

According to the present embodiment, the photo detector 5*b* includes a plurality of (preferably, a large number of) optical fibers 5*b*1 and a plurality of (preferably, a large number of) photo detection elements 5*b*2. A plurality of the optical fibers 5*b*1 are respectively provided corresponding to a plurality of positions of the incident surface 5*a*1. A plurality of the photo detection elements 5*b*2 are respectively provided corresponding to the plurality of optical fibers 5*b*1. In other words, light emitted from the scintillator 5*a* by the reflected neutrons incident on each position on the incident surface 5*a*1 is detected, through the optical fiber 5*b*1 corresponding to this position, by the photo detection element 5*b*2 corresponding to this optical fiber 5*b*1. In this configuration, a pulse neutron beam incident on the inspection target 1 and reflected neutrons can be hardly incident on the photo detection element 5*b*2, and thus, the photo detector 5*b* can be prevented from being damaged due to the neutrons.

In an example, one end of each optical fiber 5*b*1 is attached to a surface on a side opposite to the incident surface 5*a*1. In this case, when seen from a direction perpendicular to the incident surface 5*a*1, the one end of each optical fiber 5*b*1 is at the same position as the position on the incident surface 5*a*1 corresponding to the optical fiber 5*b*1. The incident surface 5*a*1 is preferably a plane.

As illustrated in FIG. 2A, the scintillator 5*a* may be disposed in an area (hereinafter, referred to as a passage area) through which a pulse neutron beam passes toward the inspection target 1 from the neutron source 3. In this case, the pulse neutron beam from the neutron source 3 is incident on the inspection target 1 through the scintillator 5*a*.

Figure 2B:
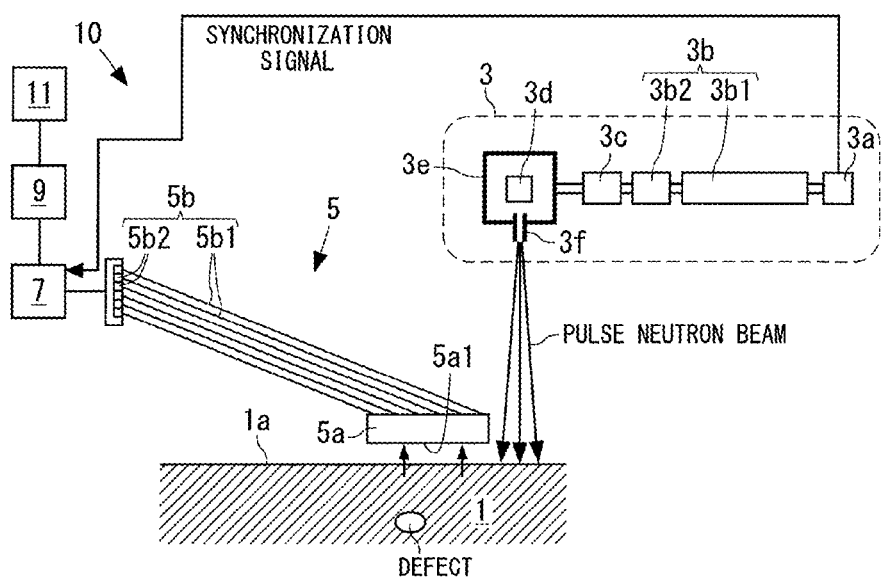
FIG. 2B illustrates another configuration of the non-destructive inspection device according to the embodiment of the present invention.

As another option, the scintillator 5*a* may be disposed away from the passage area so as to be positioned (preferably, adjacent to the passage area) in the vicinity of the passage area of the pulse neutron beam, as illustrated in FIG. 2B. In this case, the other respects of the non-destructive inspection device 10 may be the same as those in the case of FIG. 2A. With regard to FIG. 2B, neutrons, radiated from the neutron source 3, before being incident on the inspection target 1 have high energy. The scintillator 5*a* is away from the passage area of the pulse neutron beam constituted by neutrons, and thus, the scintillator 5*a* can be prevented from being damaged due to the pulse neutron beam (however, in a case where there is a low possibility that such a damage occurs, the arrangement illustrated in FIG. 2A may be used).

In this case, the scintillator 5*a* is disposed in the vicinity of the passage area (e.g., disposed adjacent to the passage area), and thus, a sufficient number of reflected neutrons are incident on the scintillator 5*a*. Therefore, presence or absence of a defect inside the inspection target 1 can be inspected on the basis of detection number data expressing the number of reflected neutrons detected by the scintillator 5*a* with respect to time.

The measurement device 7 measures the number (hereinafter, simply referred to as the detection number) of reflected neutrons that are detected by the neutron detection device 5 (e.g., at each of continuous time points of measurement) while measuring an elapsed time. More specifically, the measurement device 7 measures the number of times of light emission detected by the photo detection element 5*b*2, as the detection number of reflected neutrons, for each photo detection element 5*b*2 while measuring an elapsed time, and generates detection number data expressing the detection number with respect to the measured elapsed time. In other words, the detection number data is generated for each photo detection element 5*b*2.

Here, the detection number data is data in which each time point of measurement at and after a first time point when the neutron source 3 starts to radiate a pulse neutron beam to the inspection target 1 is associated with the detection number at this time point of measurement. In the present patent application, the respective time points of measurement mean minute time periods that are continuous with each other without intervals with respect to an elapsed time. The minute time period is preferably a time period (e.g., 50 microseconds) shorter than 100 microseconds, but the minute time period is not limited thereto as long as the detection of a defect is not hindered.

In this manner, on the basis of the detection number data obtained by the measurement device 7 with the time resolution, a defect can be detected with a high positional resolution.

In the present embodiment, by using the neutron detector 5*a* (e.g., a scintillator or a PSD described later), the neutron detection device 5 detects reflected neutrons for each position on the two-dimensional incident surface 5*a*1 (e.g., the surface along the surface 1*a*) that intersects (e.g., is perpendicular to) an advancement direction of the pulse neutron beam toward the surface 1*a* of the inspection target 1. Then, the measurement device 7 generates the above-described detection number data for each position in the two-dimensional coordinate plane. Hereinafter, the detection number data may mean detection number data for each position in the two-dimensional coordinate plane.

The neutron source 3 starts to radiate a pulse neutron beam at the first time point, and preferably, almost (or completely) stops the radiation of the neutron beam in a duration (e.g., a time equal to or less than one third of a set time) that is shorter than the set time from the first time point to a second time point described later. This duration of the pulse of the neutron beam is shorter than, for example, 0.1 milliseconds as described above. Thus, the neutron source 3 starts to radiate one pulse of a neutron beam at the first time point, and stops this pulse before the second time point. The detection number data may be the data up to the time point at which the detection number becomes so small (e.g., zero) as not to affect the determination of presence or absence of a defect. In an example, the neutron source 3 repeatedly and intermittently radiates a pulse neutron beam whose pulse time width (i.e., the duration) is 30 microseconds for example. An interval of the repeated radiation is set to be sufficiently longer than the pulse time width of the pulse neutron beam, and is sufficiently longer than the set time from the first time point to the second time point, and may be 10 milliseconds, for example.

On the basis of the detection number data generated by the measurement device 7, the calculation device 9 obtains an integrated value of the detection numbers at and after the second time point that arrives by elapse of the set time from the first time point at which the neutron source 3 starts to radiate a pulse neutron beam to the inspection target 1. The second time point is set as described later. The integrated value is an integrated value up to the time point at which the detection number becomes so small (e.g., zero) as not to affect the determination of presence or absence of a defect.

For each photo detection element 5*b*2 described above, the detection number data is generated by the measurement device 7, and on the basis of this detection number data, the integrated value corresponding to the photo detection element 5b2 is obtained by the calculation device 9. The thus-obtained integrated value for each photo detection element 5b2 may be stored in a storage device. The integrated value for each photo detection element 5b2 may be, directly from the calculation device 9 or through the storage device, displayed on a display or printed on a sheet.

Figure 3:
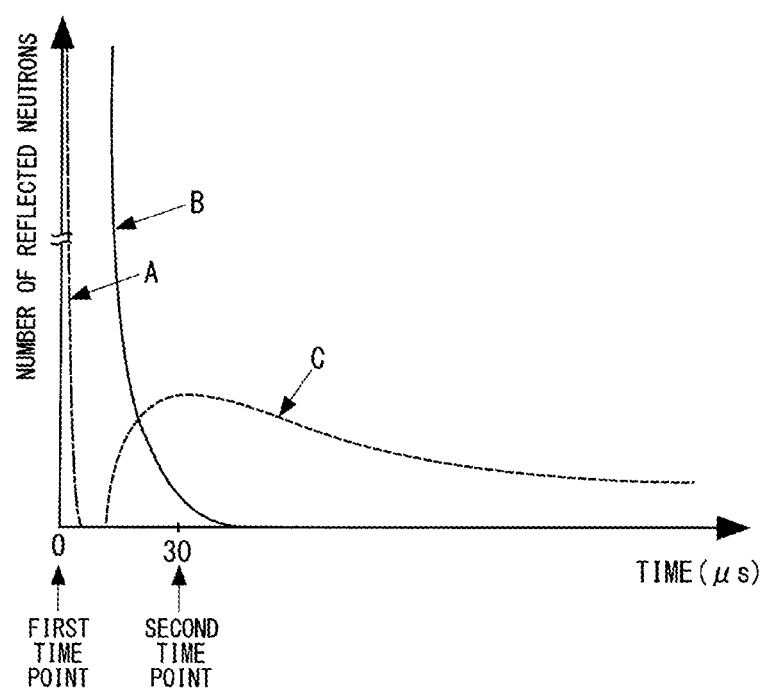
FIG. 3 illustrates the detection number of reflected neutrons with respect to time.

FIG. 3 is a diagram illustrating the setting of the second time point. A graph of FIG. 3 illustrates the number of reflected neutrons with respect to time. FIG. 3 is obtained by simulation. In FIG. 3, the horizontal axis represents an elapsed time, and a starting time point of the measurement (i.e., the origin of the horizontal axis) of the elapsed time is the first time point at which the neutron source 3 starts to radiate a pulse neutron beam to the inspection target 1. In FIG. 3, the vertical axis represents the number of reflected neutrons returned from the surface 1a. In FIG. 3, a curve A of the one-dot chain line expresses the number of neutrons radiated to the inspection target 1 by the neutron source 3. In FIG. 3, a curve B of the solid line expresses the generated number of reflected neutrons having energy higher than a set value (here, $2 \times 10^{-1}$ eV), and a curve C of the broken line expresses the generated number of reflected neutrons having energy equal to or less than the set value.

As illustrated in FIG. 3, at least most (a proportion of 50% to 90%, e.g., 80%) of the reflected neutrons having energy higher than the set value are detected by the second time point when a predetermined time (e.g., 30 microseconds) elapses from the first time point. In other words, a large number of neutrons incident on the inspection target 1 tend to be mostly returned at an early stage up to the second time point, when scattered in a hard substance (e.g., asphalt, concrete, metal, and the like) in an area where no defects exist in the inspection target 1.

Meanwhile, most of reflected neutrons (e.g., thermal neutrons) having energy equal to or less than the above-described set value are detected at and after the second time point.

The set value may be a fixed value within a range from $1.0 \times 10^{-3}$ eV to $1.0 \times 10^5$ eV, may be preferably a fixed value within a range from $1.0 \times 10^{-2}$ eV to $1.0 \times 10^3$ eV, and may be more preferably a fixed value (e.g., $2 \times 10^{-1}$ eV) within a range from $0.5 \times 10^{-1}$ eV to $1.0 \times 10$ eV.

Thereby, presence or absence of a defect (a water portion or a cavity) inside the inspection target 1 can be determined as follows.

Most of the reflected neutrons that are detected at and after the second time point are low-energy neutrons (e.g., thermal neutrons) having relatively low energy. Neutrons easily react with water. Accordingly, in a case where a portion containing water exists inside the inspection target 1, most of the reflected neutrons from this portion are low-energy neutrons. For this reason, when the above-described integrated value is larger than the above-described standard value, it can be determined that a defect portion containing water exists inside the inspection target 1.

Meanwhile, regarding a case where a cavity exists inside the inspection target 1, neutrons hardly lose energy through the cavity. Accordingly, when the integrated value of the numbers of reflected neutrons (e.g., low-energy thermal neutrons) that are detected at and after the second time point is smaller than the above-described standard value, it can be determined that a cavity exists at the position.

For this reason, the second time point is set by the following method (1), (2), or (3). The second time point may be set experimentally or by simulation for each type of inspection target 1 by the method (1) to (3). The calculation device 9 obtains an integrated value (total value) of the numbers of reflected neutrons detected by the neutron detection device 5 at and after the second time point that is set by the method (1), (2), or (3).

Assuming that the reflected neutrons are included in a pulse neutron beam radiated to the inspection target 1 at the first time point, and have been scattered in the inspection target 1 and returned, the number of the reflected neutrons that have energy equal to or less than the above-described set value is set to be S, and the number of the reflected neutrons that have energy larger than the set value is set to be N. The second time point is set such that $S^2/N$ becomes the maximum value or becomes a value close to the maximum value.

Assuming that the reflected neutrons are included in a pulse neutron beam radiated to the inspection target 1 at the first time point, and have been scattered in the inspection target 1 and returned, the second time point is set such that a predetermined proportion or more of the reflected neutrons (e.g., reflected neutrons having energy higher than that of thermal neutrons) that have energy greater than the set value occur during a period from the first time point to the second time point. Here, the predetermined proportion may be a fixed proportion within a range from 50% to 100%, preferably a fixed proportion within a range from 60% to 100%, and more preferably a fixed proportion within a range from 70% to 98%.

Assuming that the reflected neutrons are included in a pulse neutron beam radiated to the inspection target 1 at the first time point, and have been scattered in the inspection target 1 and returned, the second time point is set such that a predetermined proportion or more of the reflected neutrons (e.g., thermal neutrons) that have energy equal to or less than the set value occur at and after the second time point. Here, the predetermined proportion may be a fixed proportion within a range from 10% to 98%, preferably a fixed proportion within a range from 20% to 98%, more preferably a fixed proportion within a range from 50% to 98%, and still more preferably fixed proportion within a range from 70% to 98%.

Figure 4:
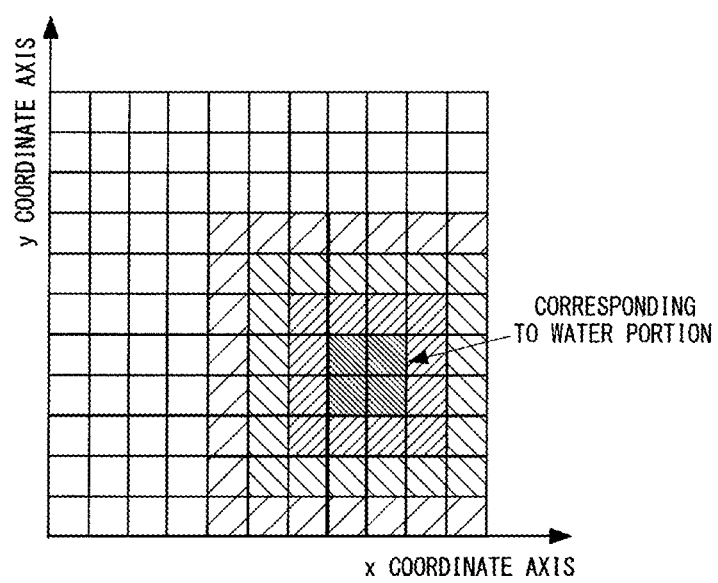
FIG. 4 illustrates data expressing a plurality of integrated values corresponding to a plurality of photo detection elements within a two-dimensional coordinate area.

FIG. 4 illustrates data expressing a plurality of integrated values corresponding to a plurality of photo detection elements 5b2 in a two-dimensional coordinate area. Preferably, integrated values based on the number of times of detection of light emission by the plurality of photo detection elements 5b2 may be displayed on a display or may be printed on a sheet, as data in which the respective integrated values are expressed by the numerical values thereof, shades or colors or patterns (in FIG. 4, densities of displayed oblique lines) depending on the numerical values, or the like, respectively at a plurality of positions (small squares in this drawing) in a two-dimensional coordinate area, as illustrated in FIG. 4, for example. The arrangement of a plurality of the positions in the two-dimensional coordinate area may be the same as the arrangement of a plurality of the photo detection elements 5b2 respectively corresponding to a plurality of the positions. The arrangement of a plurality of the photo detection elements 5b2 is the same as the arrangement of a plurality of positions on the incident surface (surface 1a) of the inspection target 1 that respectively correspond to a plurality of the photo detection elements 5b2. In FIG. 4, an integrated value is larger at a position (small square) having a higher density of displayed oblique lines, and a portion having the highest density corresponds to a water portion in the inspection target 1. The non-destructive inspection device 10 may include a data processing device 11 that generates data in which a plurality of integrated values respectively corresponding to a plurality of the photo detection elements 5b2 are expressed in a two-dimensional coordinate area as illustrated in FIG. 4.

In addition to or instead of this function, the data processing device 11 may include the following functions. The data processing device 11 determine whether or not the integrated value is smaller than the standard value for cavity, for each position (e.g., each photo detection element 5b2). When determining that the integrated value is smaller than the standard value for cavity, the data processing device 11 determines that a cavity exists in the inspection target and outputs a signal indicating existence of the cavity. This signal may be audio signal, or a specific notice indicating a position on a two-dimensional map (such as the two-dimensional coordinate area illustrated in FIG. 4) and displayed on a display, but is not limited thereto. The data processing device 11 determine whether or not the integrated value is larger than the standard value for water, for each position (e.g., each photo detection element 5b2). When determining that the integrated value is larger than the standard value for water, the data processing device 11 determines that water exists in the inspection target and outputs a signal indicating existence of the water. This signal may be audio signal, or a specific notice indicating a position on a two-dimensional map (such as the two-dimensional coordinate area illustrated in FIG. 4) and displayed on a display, but is not limited thereto.

The neutron source 3 described above can be configured to have such a small size that the neutron source can be mounted on a vehicle such as a truck. Therefore, it is possible to inspect whether or not a defect exists, for example, inside a runway of an airport, a road of a car, or a tunnel structure (a structure for forming a tunnel) as the inspection target 1 by the non-destructive inspection device 10 while a vehicle such as a truck are moving in a state where the non-destructive inspection device 10 described above is mounted on the vehicle.

In a non-destructive inspection method using the non-destructive inspection device 10 according to this embodiment, a pulse neutron beam is made to be incident on the surface 1a of the inspection target 1 by the neutron source 3, and thus reflected neutrons (scattered neutrons) that have been scattered in the inspection target 1 and returned are detected by the neutron detection device 5. The measurement device 7 measures the detection number of the reflected neutrons, and generates detection number data expressing the detection number with respect to time.

Example Based on Simulation

FIGS. 5A to 5F illustrate integrated values of the numbers of reflected neutrons that are obtained by simulation. In FIGS. 5A to 5F, the horizontal axis and the vertical axis are coordinate axes perpendicular to a direction of a pulse neutron beam. In this example, a numerical value or a numerical range expressed in each region in a two-dimensional coordinate area illustrated in each of FIGS. 5A to 5F indicates an integrated value of the numbers of reflected neutrons detected at each position in the region or a range of the integrated value when a pulse neutron beam is made to be radially incident on the inspection target 1 from the neutron source 3. Each numerical range is normalized by setting, as a value of 1, an integrated value when the pulse neutron beam is made to be incident on the inspection target 1 having no defects.

Figure 5A:
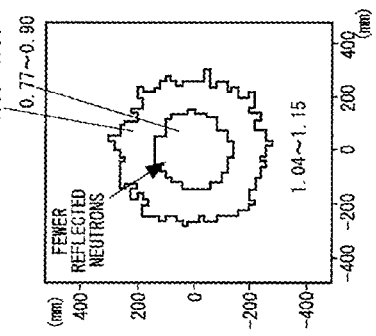
FIGS. 5A to 5F illustrate data expressing integrated values of the numbers of reflected neutrons that are obtained by simulation.
Figure 5B:
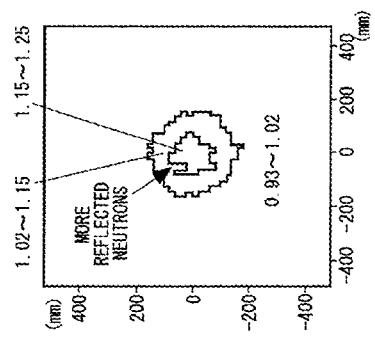
Figure 5C:
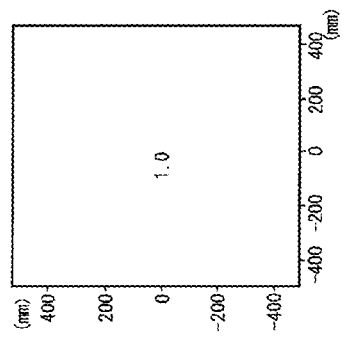

In more detail, in each of FIGS. 5A to 5C, a numerical value or a numerical range expressed in each region is an integrated value of the numbers of reflected neutrons having energy equal to or less than $2\times10^{-1}$ eV, or a range of the integrated value, on the assumption that a pulse neutron beam is made to be incident on the inspection target 1 from the neutron source 3 at the first time point, and the reflected neutrons thereby occurs at and after the first time point.

Figure 5D:
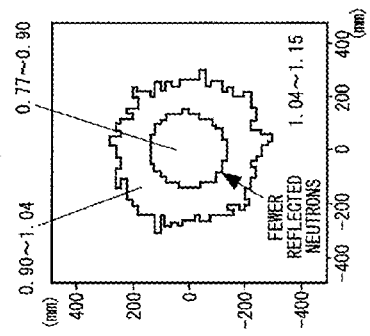
Figure 5E:
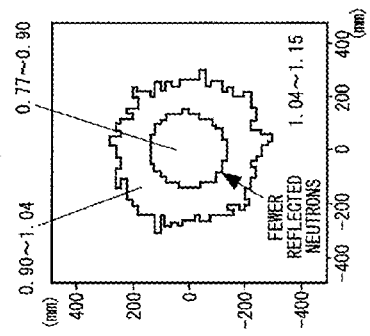
Figure 5F:
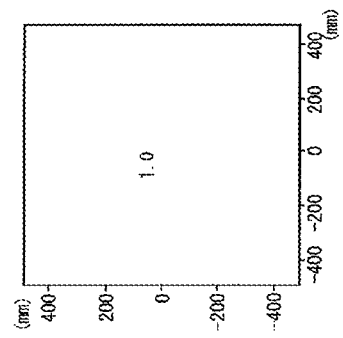

In each of FIGS. 5D to 5F, a numerical value or a numerical range expressed in each region is an integrated value of the numbers of reflected neutrons occurring at and after the second time point, or a range of the integrated value, on the assumption that a pulse neutron beam is made to be incident on the inspection target 1 from the neutron source 3 at the first time point, and the reflected neutrons thereby occurs.

The center of the two-dimensional coordinate area illustrated in each of FIGS. 5A to 5F corresponds to the position of the pulse neutron beam incident on the inspection target 1.

FIGS. 5A to 5D illustrate a case where a pulse neutron beam is made to be incident on the inspection target 1 having no defects. Accordingly, in FIG. 5A, integrated values at the respective positions are the same value of 1.0.

FIGS. 5B and 5E illustrate a case where a pulse neutron beam is made to be incident on a defect portion containing water in the inspection target 1. In each of FIGS. 5B and 5E, an integrated value in the central region is larger than integrated values in other regions in the same drawing and the integrated value at each position in FIGS. 5A and 5D. Accordingly, it can be understood that a defect portion containing water exists in the central region in each of FIGS. 5B and 5E.

FIGS. 5C and 5F illustrate a case where a pulse neutron beam is made to be incident on a defect portion including a cavity in the inspection target 1. In each of FIGS. 5C and 5F, an integrated value in the central region is smaller than integrated values in other regions of the same drawing and the integrated value in FIGS. 5A and 5D. Accordingly, it can be understood that a defect portion including a cavity exists in the central region in FIGS. 5C and 5F.

FIGS. 6A to 6F illustrate integrated values of the numbers of reflected neutrons that are obtained by simulation, and illustrates a case where a position of a pulse neutron beam incident on the inspection target 1 is shifted from a defect portion in the inspection target 1. Respects that are not described below with regard to FIGS. 6A to 6F are the same as those in the case of FIGS. 5A to 5F.

Figure 6A:
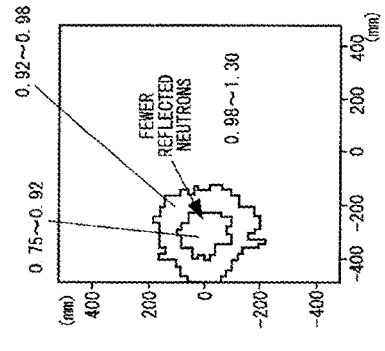
FIGS. 6A to 6F illustrate another data expressing integrated values of the numbers of reflected neutrons that are obtained by simulation.
Figure 6B:
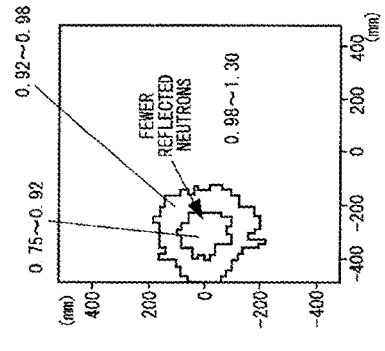
Figure 6C:
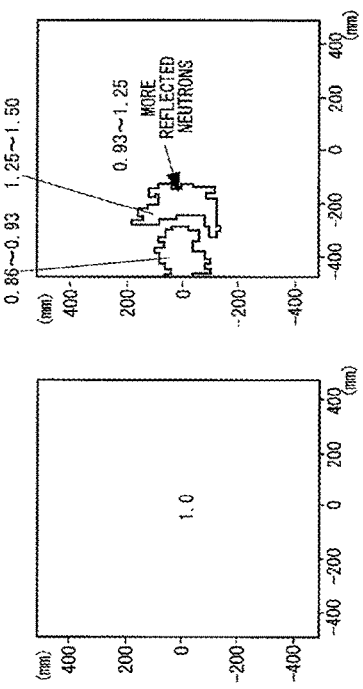

In each of FIGS. 6A to 6C, a numerical value or a numerical range illustrated in each region in a two-dimensional coordinate area in the drawing is an integrated value of the numbers of reflected neutrons having energy equal to or less than $2\times10^{-1}$ eV, or a range of the integrated value, on the assumption that a pulse neutron beam is made to be incident on the inspection target 1 from the neutron source 3 at the first time point, and the reflected neutrons thereby occurs at and after the first time point.

Figure 6D:
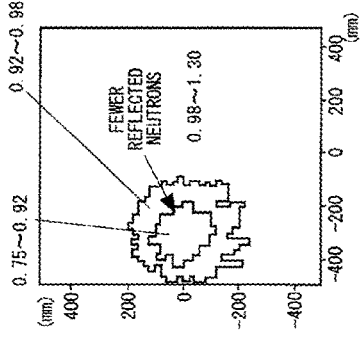
Figure 6E:
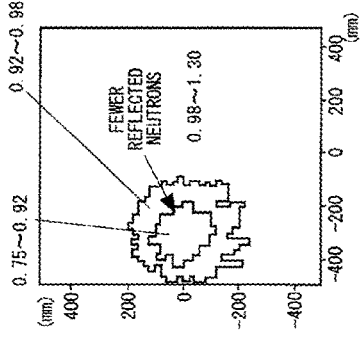
Figure 6F:
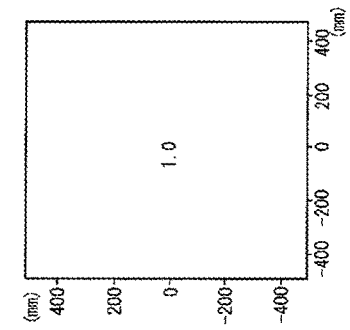

In each of FIGS. 6D to 6F, a numerical value or a numerical range illustrated in each region in a two-dimensional coordinate area in the drawing is an integrated value of the numbers of reflected neutrons, or a range of the integrated value, on the assumption that a pulse neutron beam is made to be incident on the inspection target 1 from the neutron source 3 at the first time point, and the reflected neutrons thereby occurs at and after the second time point.

Each numerical range is normalized by setting, as a value of 1, an integrated value when the pulse neutron beam is made to be incident on the inspection target 1 having no defects.

In each of FIGS. 6A to 6F, the center of the two-dimensional coordinate area corresponds to the position of the pulse neutron beam. In FIGS. 6B, 6C, 6E and 6F, a portion corresponding to a position slightly shifted to the left from the center of the two-dimensional coordinate area is the position of a defect portion in the inspection target 1.

FIGS. 6A and 6D illustrate a case where a pulse neutron beam is made to be incident on the inspection target 1 having no defects. Accordingly, in FIG. 6A, an integrated value at each position is the same value of 1.0.

In each of FIGS. 6B and 6E, an integrated value in a region slightly shifted to the left side from the central portion thereof is larger than integrated values in other regions of the same drawing and an integrated value at each position in FIGS. 6A and 6D. Accordingly, it can be understood that a defect portion containing water exists in the region slightly shifted to the left side from the central portion of FIGS. 6B and 6E.

In each of FIGS. 6C and 6F, an integrated value in a region shifted to the left side from the central portion thereof is smaller than integrated values in other regions of the same drawing and integrated values in FIGS. 6A and 6D. Accordingly, it can be understood that a defect portion including a cavity exists in the region shifted to the left side from the central portion in FIGS. 6C and 6F.

[Simulation]

Figure 7A:
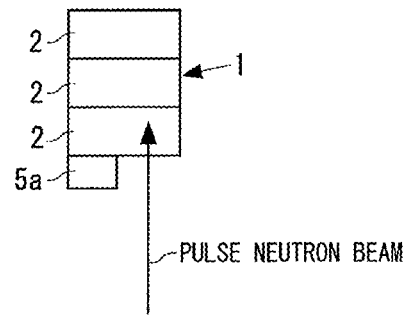
FIG. 7A illustrates a positional relation among a pulse neutron beam, an inspection target, and a scintillator.
Figure 7B:
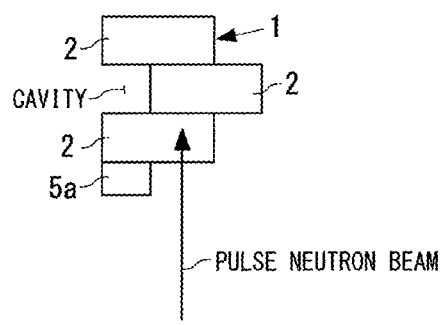
FIG. 7B illustrates another positional relation among the pulse neutron beam, the inspection target, and the scintillator.
Figure 7C:
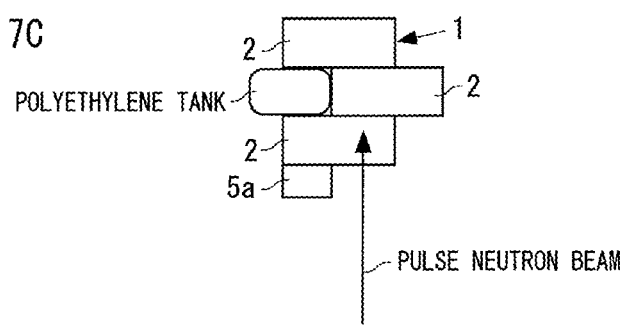
FIG. 7C illustrates still another positional relation among the pulse neutron beam, the inspection target, and the scintillator.

FIGS. 7A to 7C each illustrate a positional relation among a pulse neutron beam by the non-destructive inspection device 10 described above, the inspection target 1, and the scintillator 5a. In each of FIGS. 7A to 7C, the scintillator 5a is disposed so as to be adjacent to a passage area of the pulse neutron beam to the inspection target 1 from the neutron source 3. In each of FIGS. 7A to 7C, the inspection target 1 is constituted by three concrete blocks 2. Each of the blocks 2 has a thickness of 30 cm. In FIG. 7A, the inspection target 1 having no defects is formed by the blocks 2. In FIG. 7B, the inspection target 1 having a cavity therein is formed by the blocks 2. In FIG. 7C, a polyethylene tank filled with water is interposed between the two blocks 2 so that the inspection target 1 having a water portion therein is formed by the blocks 2.

Regarding the cases of FIGS. 7A to 7C, the above-described integrated values were obtained by simulation. Results thereof are illustrated in FIGS. 8A to 8C. The results of FIGS. 8A to 8C correspond to the cases of FIGS. 7A to 7C, respectively. In each of FIGS. 8A to 8C, the horizontal axis and the vertical axis are coordinate axes perpendicular to a direction of the pulse neutron beam in FIGS. 7A to 7C. A numerical value or a numerical range expressed in each region in a two-dimensional coordinate area illustrated in each of FIGS. 8A to 8C indicates an integrated value of the numbers of reflected neutrons detected at each position in the region, or a range of the integrated value. Each numerical range is normalized by setting, as a value of 1, an integrated value when the pulse neutron beam is made to be incident on the inspection target 1 having no defects.

The center of the two-dimensional coordinate area illustrated in each of FIGS. 8A to 8C corresponds to the position of the scintillator 5a.

FIG. 8A illustrates the case of FIG. 7A in which a defect does not exist, and thus, integrated values at the respective positions in FIG. 8A are the same value of 1.0.

FIG. 8B illustrates the case of FIG. 7B in which a cavity exists, and thus, integrated values in the respective regions in FIG. 8B are equal to or less than the integrated value in each region in FIG. 8A.

FIG. 8C illustrates the case of FIG. 7C in which a water portion exists, and thus, integrated values in the respective regions in FIG. 8C are equal to or larger than the integrated value in each position in FIG. 8A.

First Example Based on Experiment

Figure 9A:
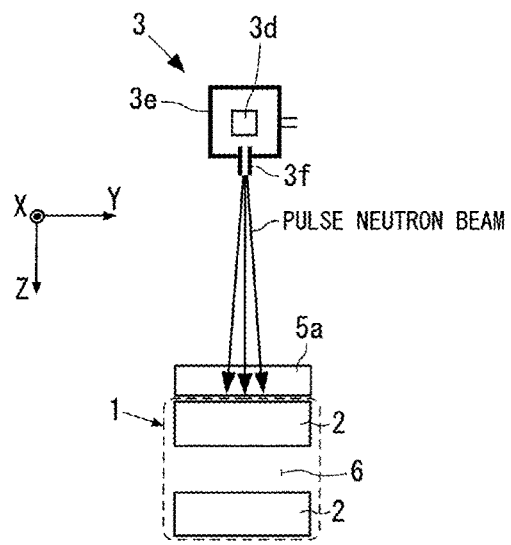
FIG. 9A illustrates a configuration of a first example based on experiment.

FIG. 9A illustrates a positional relation among the neutron source 3 of the non-destructive inspection device 10, the scintillator 5a, and the inspection target 1 in a first example. As illustrated in FIG. 9A, two concrete blocks 2 that are rectangular parallelepipeds were prepared as the inspection target 1.

In FIG. 9A, the XYZ coordinate system is a coordinate system for representing dimensions of the inspection target 1. In FIG. 9A, dimensions in the X-axis direction, the Y-axis direction, and the Z-axis direction of each of the blocks 2 are 300 mm, 300 mm, and 100 mm, respectively.

A space 6 having a dimension in the Z-axis direction of 100 mm was provided between the two blocks 2, and inspection was performed for the following cases 1 to 4.

(Case 1) Nothing is disposed in the space 6.

(Case 2) The space 6 is completely filled with a concrete block. Dimensions in the X-axis direction, the Y-axis direction, and the Z-axis direction of the block are 300 mm, 300 mm, and 100 mm, respectively.

(Case 3) A polyethylene tank filled with water is disposed in the space 6. Dimensions in the X-axis direction, the Y-axis direction, and the Z-axis direction of the polyethylene tank are approximately 300 mm, 300 mm, and 75 mm to 80 mm, respectively.

(Case 4) The space 6 is completely filled with acrylic block. Dimensions in the X-axis direction, the Y-axis direction, and the Z-axis direction of the block are 300 mm, 300 mm, and 100 mm, respectively.

Figure 9B:
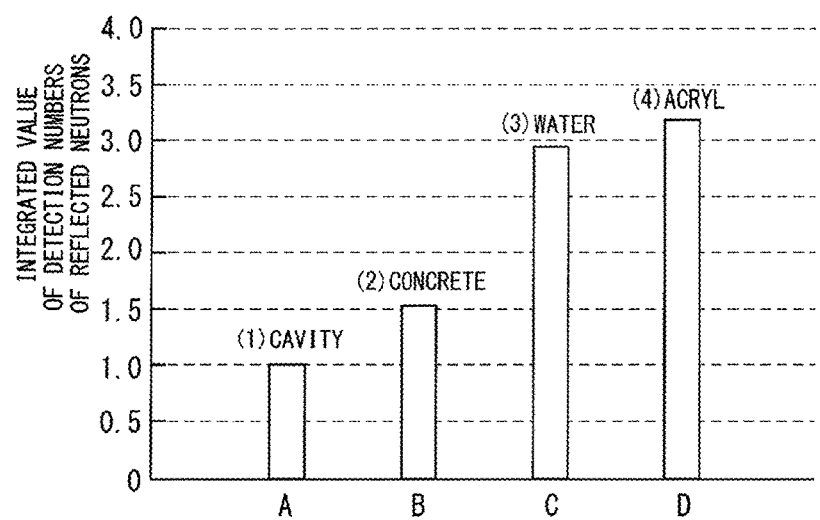
FIG. 9B illustrates a measurement result in the first example.

FIG. 9B illustrates the above-described integrated values measured for the cases 1 to 4, respectively. Here, the integrated value is a value obtained by integrating the number of reflected neutrons detected by a specific photo detection element 5b2 at and after the second time point. A time range over which the integration is performed is a range between the second time point (a time point after 0.31 milliseconds from the first time point that is a time point when a pulse neutron beam is radiated) and a time point (a time point after 0.62 milliseconds from the first time point) when the measurement is ended. The vertical axis in FIG. 9B represents a value that is normalized by setting, as a value of 1, the integrated value in the case 1. In FIG. 9B, bar graphs A to D indicate the cases 1 to 4, respectively.

As illustrated in FIG. 9B, in the case 1 where a cavity exists inside the concrete, the integrated value is smaller than that in the case 2 where a cavity does not exist inside the concrete.

In the case 3 where water is contained in the concrete, the integrated value is larger than that in the case 2.

Accordingly, it can be understood that presence of a cavity and water in the concrete can be detected on the basis of the measured integrated value.

Regarding the case 4, a density of hydrogen in acryl is substantially the same as a density of hydrogen in water, and a neutron easily reacts with hydrogen. For this reason, in the case 4 where the acrylic block is used, the integrated value is substantially the same as that in the case 3 where water is contained. In other words, acryl can be regarded as water.

Second Example Based on Experiment

Figure 10A:
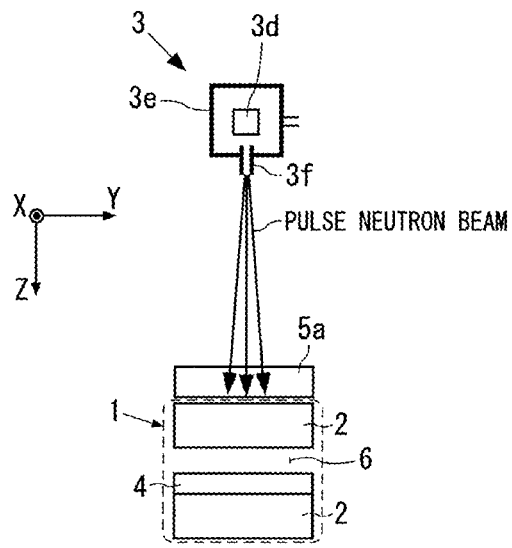
FIG. 10A illustrates a configuration of a second example based on experiment.

FIG. 10A illustrates a positional relation among the neutron source 3 of the non-destructive inspection device 10, the scintillator 5a, and the inspection target 1 in a second example. As illustrated in FIG. 10A, two concrete blocks 2 that are rectangular parallelepipeds were prepared as the inspection target 1.

In FIG. 10A, the XYZ coordinate system is a coordinate system for representing dimensions of the inspection target 1. In FIG. 10A, dimensions in the X-axis direction, the Y-axis direction, and the Z-axis direction of each of the blocks 2 are 300 mm, 300 mm, and 100 mm, respectively.

The space 6 having a dimension in the Z-axis direction of 100 mm was provided between the two blocks 2. An acrylic block 4 regarded as water as described above was disposed in the space 6. Dimensions in the X-axis direction and the Y-axis direction of the acrylic block 4 were 300 mm and 300 mm, respectively, and inspection was performed with a thickness (i.e., a dimension in the Z-axis direction) of the acrylic block 4 being changed.

Figure 10B:
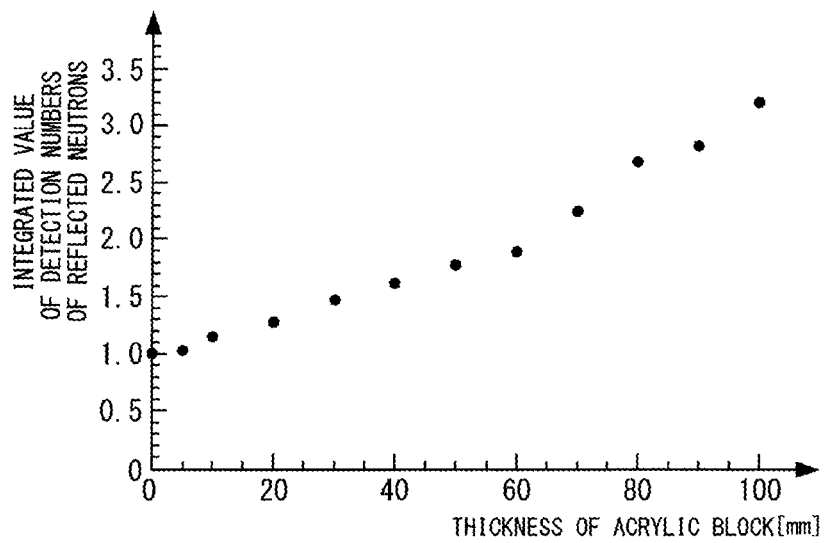
FIG. 10B illustrates a measurement result in the second example.

In FIG. 10B, the horizontal axis represents a thickness of the acrylic block 4, and the vertical axis represents a measured integrated value. Here, the integrated value represented by the vertical axis is normalized by setting, as a value of 1, an integrated value in the case where nothing exists in a cavity 6. The integrated value is a value obtained by integrating the number of reflected neutrons detected by a specific photo detection element 5b2 at and after the second time point. A time range in which the integration is performed is a range between the second time point (a time point after 0.31 milliseconds from the first time point) and a time point (a time point after 0.62 milliseconds from the first time point) when the measurement is ended. In FIG. 10B, a black circles indicates the measured integrated values.

As understood from FIG. 10B, in the case where water is accumulated in the cavity inside the concrete, the integrated value changes depending on a volume ratio of water to the cavity. Accordingly, for example, in a case where a size of a cavity can be known in advance, it is possible to obtain an amount of water in the cavity.

Third Example Based on Experiment

Figure 11A:
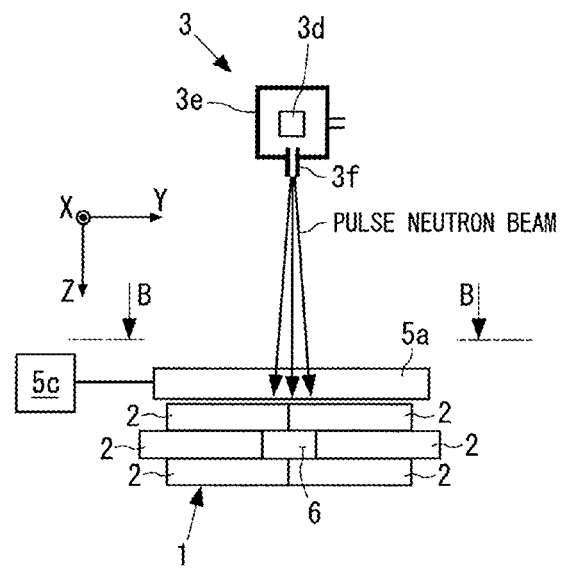
FIG. 11A illustrates a configuration of a third example based on experiment.

FIG. 11A illustrates a positional relation among the neutron source 3 of the non-destructive inspection device 10, the neutron detector 5a, and the inspection target 1 in a third example. The inspection target 1 is a combination of six concrete blocks 2 that are rectangular parallelepipeds as illustrated in FIG. 11A. The space 6 is formed inside the inspection target 1. The space 6 is used as a cavity, or the acrylic block 4 (see FIGS. 12A to 12E described later) that is a rectangular parallelepiped having substantially the same dimensions as those of the space 6 is disposed in the space 6. A pulse neutron beam is made to be incident on the inspection target 1 from the neutron source 3, and reflected neutrons thereof are detected by the neutron detection device 5 to measure an integrated value obtained by integrating the numbers of reflected neutrons detected at and after the second time point.

In FIG. 11A, the XYZ coordinate system is a coordinate system for representing dimensions of the inspection target 1. In FIG. 11A, dimensions in the X-axis direction, the Y-axis direction, and the Z-axis direction of each of the concrete blocks 2 are 300 mm, 300 mm, and 60 mm, respectively, and dimensions (see FIGS. 12A to 12E) in the X-axis direction, the Y-axis direction, and the Z-axis direction of the acrylic block 4 (FIGS. 12A to 12E) are 300 mm, 100 mm, and 55 mm, respectively.

Figure 11B:
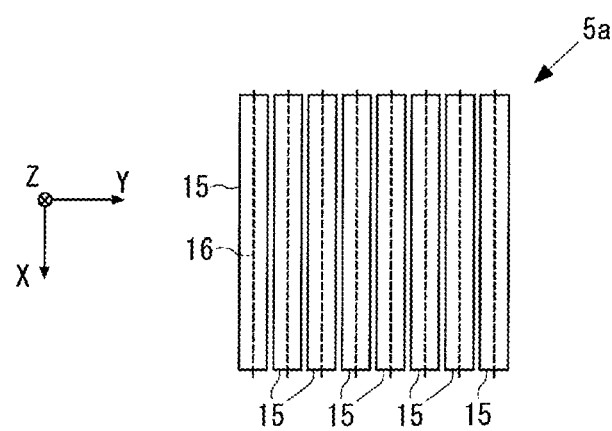
FIG. 11B is a diagram when seen from an arrow direction of the line B-B of FIG. 11A, and illustrates a neutron detector.
Figure 12A:
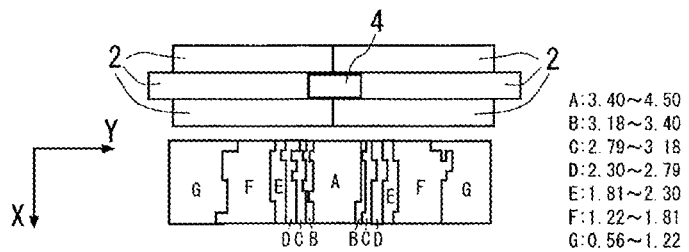
FIGS. 12A to 12E illustrate a measurement result in the third example.
Figure 12B:
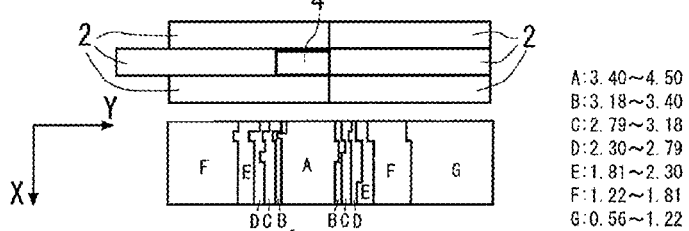
Figure 12C:
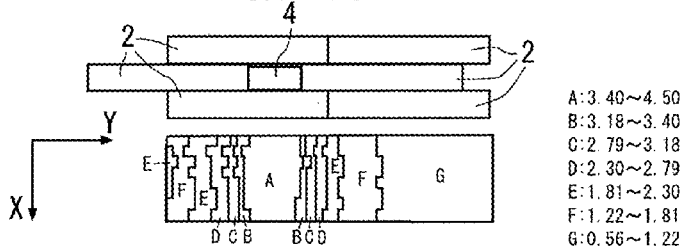
Figure 12D:
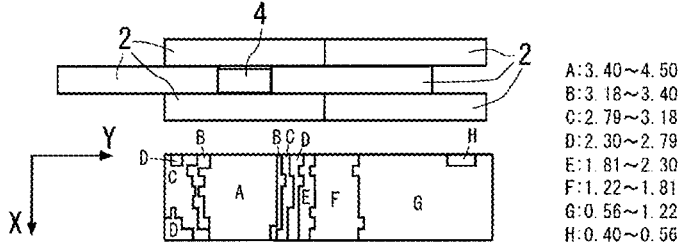
Figure 12E:
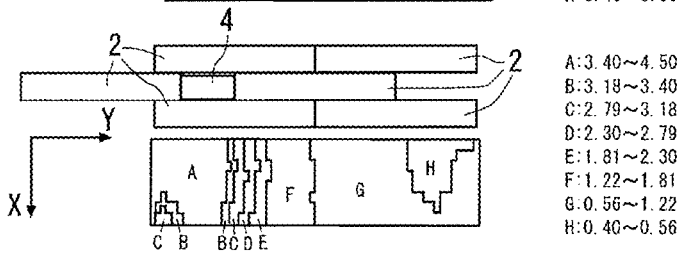
Figure 13A:
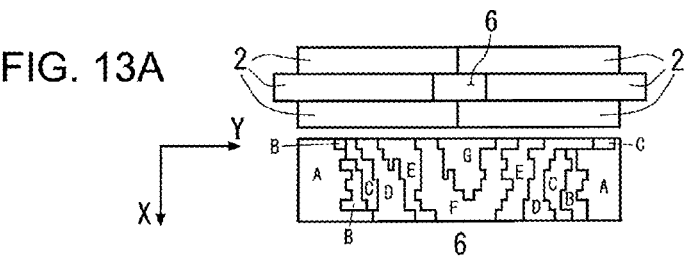
FIGS. 13A to 13E illustrate another measurement result in the third example.
Figure 13B:
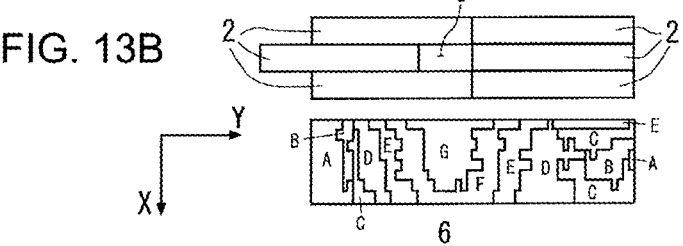
Figure 13C:
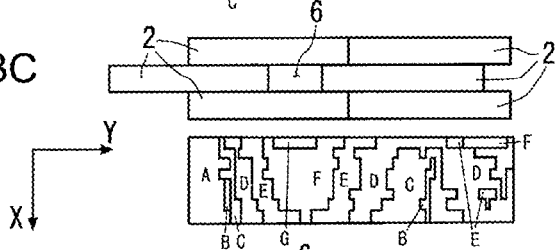
Figure 13D:
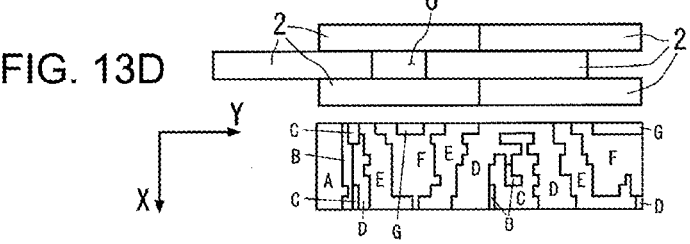
Figure 13E:
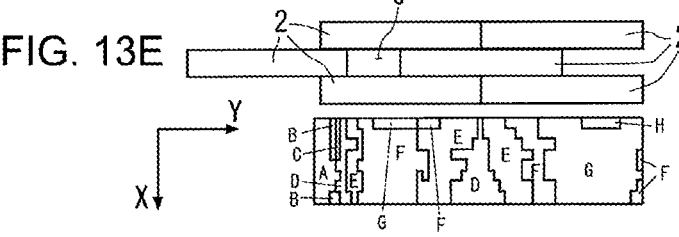

In this experiment, a position sensitive detector (PSD) was used as the neutron detector 5a. FIG. 11B is a diagram when seen from an arrow direction of the line B-B in FIG. 11A, and illustrates the PSD 5a. The PSD 5a includes a plurality of pipes 15 that are directed to the X-axis direction and are arranged in the Y-axis direction. A gas (e.g., a helium-3 gas) that reacts with neutrons is enclosed in each of the pipes 15. A core wire 16 extending in the X-axis direction is disposed within each of the pipes 15, and a voltage of 1000 V to 2000 V is applied to the core wires 16. When the neutrons arrive at the pipe 15, the gas is ionized at the position. When the length of the core wire 16 is L, the position in the X-axis direction where the neutrons arrive at the pipe is X with respect to the origin at one end of the core wire 16, and electric charges (changes in voltage) respectively generated at the both ends of the core wire 16 are Q1 and Q2, the relationship of $X/L=Q2/(Q1+Q2)$ is established.

When a PSD is used as the neutron detector 5a, the neutron detection device 5 includes a position detection unit 5c, the position detection unit 5c detects the electric charges Q1 and Q2 described above, obtains the arrival position X on the basis of the detected electric charges Q1 and Q2 and the known length L, specifies the pipe 15 in which the electric charges Q1 and Q2 are generated, and thereby obtains a two-dimensional coordinate position of a reflected neutron. The measurement device 7 can obtain detection number data for each two-dimensional coordinate position on the basis of the detection of the reflected neutrons for each two-dimensional coordinate position.

(Case of Acrylic Block)

In FIG. 11A, the acrylic block 4 was disposed in the space 6, and the positions of only the block 2 and the block 4 that are disposed in the middle in the Z-axis direction were changed in the Y-axis direction, to perform measurement. FIGS. 12A to 12E illustrate results of the measurement. In each of FIGS. 12A to 12E, an upper-side part is a partially enlarged view of FIG. 11A when the block 4 is disposed in the space 6, and illustrates the blocks 2 and the block 4. In FIGS. 12A to 12E, lower-side parts illustrate regions A to H in two-dimensional coordinate areas of which positions in the Y-axis direction are aligned to the upper-side parts, and numerical ranges of A to H at right ends indicate ranges of integrated values in the respective regions A to H.

The six blocks 2 are arrayed in two rows in the Y-axis direction and three rows in the X-axis direction, and integrated values in each of FIGS. 12A to 12E and each of FIGS. 13A to 13E described later are normalized by setting, as a value of 1, an integrated value measured in a state where neither the space 6 nor the acrylic block 4 exists in the inspection target 1.

As understood from FIGS. 12A to 12E, the integrated value becomes large at a two-dimensional coordinate position corresponding to the position of the acrylic block 4. Thus, it is confirmed that a two-dimensional position of the acrylic block 4 (i.e., water) in concrete can be specified from the integrated value.

(Case of Cavity)

In FIG. 11A, measurement was performed with the space 6 being kept as a cavity, and with a position of only the block 2 disposed in the middle in the Z-axis direction being changed in the Y-axis direction. FIGS. 13A to 13E illustrate results of the measurement. In each of FIGS. 13A to 13E, an upper-side part is a partially enlarged view of FIG. 11A, and illustrates the blocks 2 and the space 6. In FIGS. 13A to 13E, lower-side parts illustrate regions A to H in two-dimensional coordinate areas of which positions in the Y-axis direction are aligned to the upper-side parts, and numerical ranges of A to H at right ends indicate ranges of integrated values in the respective regions A to H.

As understood from FIGS. 13A to 13E, an integrated values becomes small at a two-dimensional coordinate position corresponding to the position of the cavity. Thus, it is confirmed that a two-dimensional position of the cavity can be specified from the integrated value.

Fourth Example Based on Experiment

Figure 14:
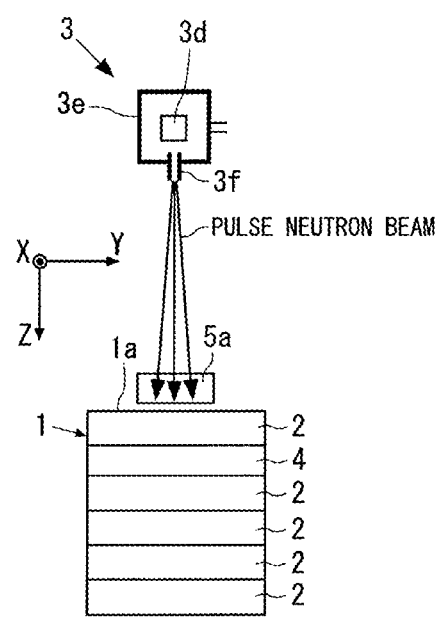
FIG. 14 illustrates a configuration of a fourth example based on experiment.

FIGS. 14 to 17 illustrate a fourth example of the non-destructive inspection device 10. FIG. 14 illustrates a positional relation among the neutron source 3 of the non-destructive inspection device 10, the neutron detector 5a, and the inspection target 1. In FIG. 14, the inspection target 1 is a combination of five concrete blocks 2 and one acrylic block 4 (or a cavity). Regarding the concrete blocks 2, the XYZ coordinate system is a coordinate system for representing dimensions of the inspection target 1 in FIG. 14. In FIG. 14, the above-described PSD was used as the neutron detector 5a.

(Case of Acrylic Block)

In FIG. 14, dimensions in the X-axis direction, the Y-axis direction, and the Z-axis direction of each of the concrete blocks 2 are 300 mm, 300 mm, and 60 mm, respectively, and dimensions (see FIG. 14A) in the X-axis direction, the Y-axis direction, and the Z-axis direction of the acrylic block 4 are 300 mm, 300 mm, and 55 mm, respectively. As illustrated in FIG. 14, these blocks are arranged in the thickness directions without gaps, a position (i.e., a depth from the surface 1a of the inspection target 1) of the acrylic block 4 in the Z-axis direction is changed, and a pulse neutron beam is radiated to the inspection target 1 from the neutron source 3 in the Z-axis direction for each depth of the acrylic block 4, to thereby measure the above-described detection number by using the PSD 5a.

Figure 15:
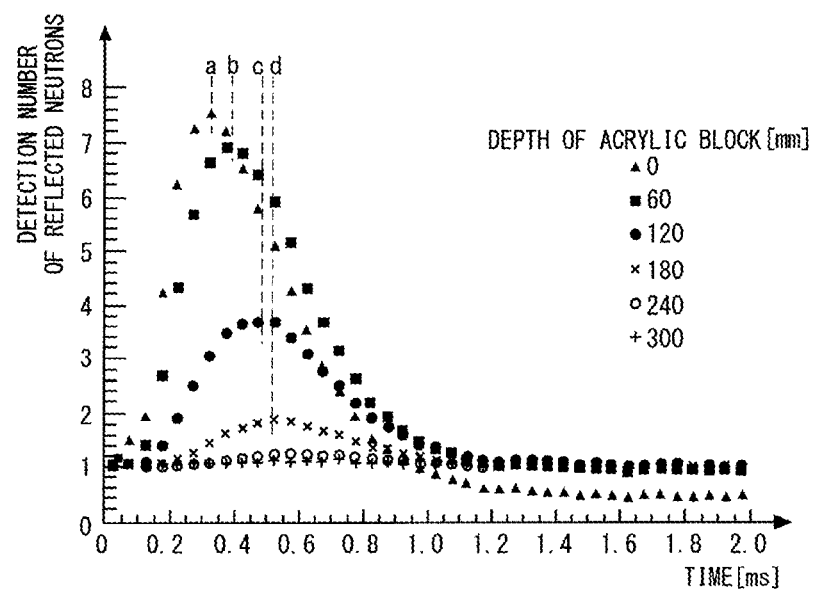
FIG. 15 illustrates a measurement result in the fourth example.

FIG. 15 illustrates measurement results. In FIG. 15, the horizontal axis represents time of which origin is the above-described first time point, and the vertical axis represents the number of reflected neutrons detected by the neutron detector 5a at a specific position in an XY coordinate system. The detection number represented by the vertical axis is normalized with time distribution of the detection numbers obtained in a standard state where the acrylic block 4 is replaced with an additional concrete block 2 in the inspection target 1. In other words, for each time point in the horizontal axis, the detection number represented by the vertical axis is normalized by setting, as a value of 1, the detection number obtained in the standard state. Accordingly, when neither a cavity nor water exists in the inspection target 1, the detection number of the vertical axis becomes 1 at each time point in the horizontal axis in FIG. 15.

In FIG. 15, triangles, squares, black circles, X marks, white circles, and cross marks respectively indicate the detection numbers in the cases of values of a depth of the acrylic block 4 that are 0 mm, 60 mm, 120 mm, 180 mm, 240 mm, and 300 mm.

In FIG. 15, the broken lines a, b, c, and d respectively indicate the respective time points of peaks of the triangles, the squares, the black circles, and the X marks. As understood from the broken lines a, b, c, and d, as a position of the acrylic block 4 (i.e., water) is deeper, the time point of the peak of the detection number is delayed. Accordingly, a depth where water exists can be detected from a time point of the peak of the detection numbers in the above-described detection number data in which each time point of measurement at and after the first time point is associated with the detection number at the time point of measurement.

Figure 16:
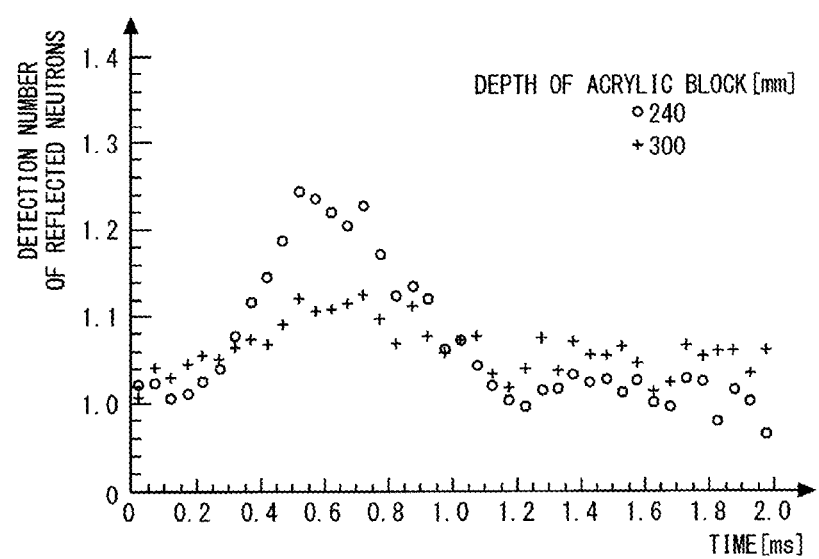
FIG. 16 illustrates a case where the vertical axis in FIG. 15 is enlarged.

FIG. 16 illustrates the white circles and the cross marks in a state of the enlarged scale of the vertical axis in FIG. 15. As understood from FIG. 16, even when values of a depth of the acrylic block 4 are 240 mm and 300 mm, the detection number is larger than 1, and thus it is understood that water existing at these depths can be detected.

(Case of Cavity)

In FIG. 14, experiment was performed with the acrylic block 4 being replaced with a cavity having the same dimensions as those of the acrylic block. In other words, a pulse neutron beam was radiated to the inspection target 1 from the neutron source 3 in the Z-axis direction for each depth of the cavity with a position (i.e., a depth from the surface 1a of the inspection target 1) of the cavity being changed in the Z-axis direction, to thereby measure the above-described detection numbers by using the PSD 5a.

Figure 17:
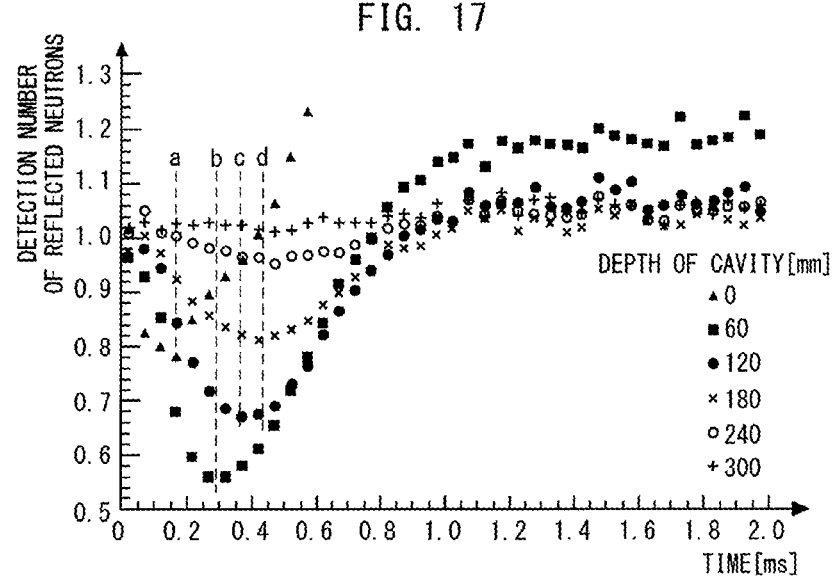
FIG. 17 illustrates another measurement result in the fourth example.

FIG. 17 illustrates measurement results. In FIG. 17, the horizontal axis represents the time of which origin is the above-described first time point (i.e., a time point when a pulse neutron beam is radiated from the neutron source 3), and the vertical axis represents the number of reflected neutrons detected by the neutron detector 5a at a specific position in an XY coordinate system. The detection number represented by the vertical axis is normalized in the same method as that in FIG. 15. In FIG. 17, triangles, squares, black circles, X marks, white circles, and cross marks respectively indicate the detection numbers in the cases of values of a depth of the cavity that are 0 mm, 60 mm, 120 mm, 180 mm, 240 mm, and 300 mm.

In FIG. 17, the broken lines a, b, c, and d respectively indicate each time point of bottoms (the lowest time point) of the triangles, the squares, the black circles, and the X marks. As understood from the broken lines a, b, c, and d, as a position of the cavity is deeper, the time point of the bottom of the detection number becomes is delayed. Accordingly, a depth where the cavity exists can be detected from a time point of the bottom of the detection numbers in the above-described detection number data in which each time point of measurement at and after the first time point is associated with the detection number at the time point of measurement.

Figure 18:
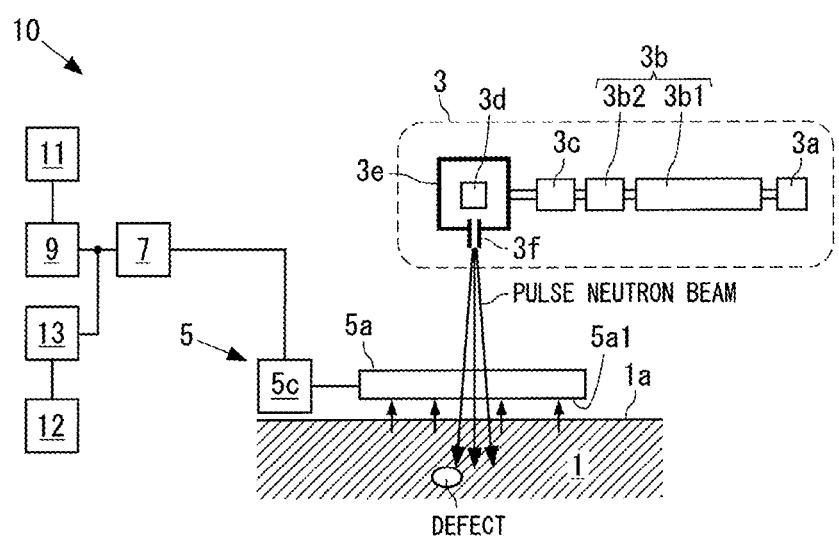
FIG. 18 illustrates a configuration of a non-destructive inspection device having a function of detecting a depth of water or a cavity.

FIG. 18 illustrates a configuration of the above-described non-destructive inspection device 10 with a function of detecting a depth of water or a cavity. In this case, the non-destructive inspection device 10 further includes a storage device 12 and a data processing device 13. In an example of FIG. 18, the neutron detection device 5 includes the PSD 5a and the position detection unit 5c described above.

The storage device 12 stores first correspondence data in which a depth (hereinafter, simply referred to as a depth) that is a length from the surface of a test object and that represents each position of water inside the test object of the same material as that of the inspection target 1 is associated with a time point of a peak of the detection numbers (at a specific position on the incident surface 5a1). The time point of the peak in the first correspondence data is a time point of a peak in time distribution of the detection numbers obtained in the condition that for each time point at and after the first time point, the detection number is expressed as a ratio to a reference value. Here, the reference value is determined for each time point, and is the detection number obtained (at a specific position on the incident surface 5a1) at the time point for the test object in a standard state where neither water nor a cavity exists therein. For each depth where water exists, the first correspondence data represents a time point of a peak of the detection numbers measured in the case where a pulse neutron beam is made to be incident on the surface of the test object by the non-destructive inspection device 10, on the assumption that water exists at the same depth. The first correspondence data is obtained by performing experiment using the non-destructive inspection device 10, on the test object including an acrylic block or water therein.

The storage device 12 may store second correspondence data instead of or in addition to the first correspondence data. The second correspondence data is data in which a depth (hereinafter, simply referred to as a depth) that is a length from the surface of a test object and that represents each position of a cavity inside the test object of the same material as that of the inspection target 1 is associated with a time point of a bottom of the detection numbers (at a specific position on the incident surface 5a1). The time point of the bottom in the second correspondence data is a time point of a bottom in time distribution of the detection numbers obtained in the condition that for each time point at and after the first time point, the detection number is expressed as a ratio to the above-described reference value. For each depth where the cavity exists, the second correspondence data represents a time point of a bottom of the detection numbers measured in the case where a pulse neutron beam is made to be incident on the surface of the test object by the non-destructive inspection device 10, on the assumption that the cavity exists at the same depth. The second correspondence data is obtained by performing experiment using the non-destructive inspection device 10, on the test object including a cavity therein.

When the first correspondence data is used, the following process is performed. The data processing device 13 specifies a time point of a peak of the detection numbers in the detection number data (that is data at each position on the incident surface 5a1 and that is data in which each time point of measurement at and after the first time point is associated with the detection number at the same time point of measurement) measured by the measurement device 7. The time point of the peak is a time point of a peak in time distribution of the detection numbers obtained in the condition that for each time point at and after the first time point, the detection number is expressed as a ratio to the above-described reference value. The data processing device 13 specifies a depth of a position of water inside the inspection target 1 on the basis of the time point of the peak and the first correspondence data stored in the storage device 12. The data processing device 13 outputs the specified depth. The output depth may be stored in an appropriate storage medium, may be displayed on a display, or may be printed on a sheet.

When the second correspondence data is used, the following process is performed. The data processing device 13 specifies a time point of a bottom of the detection numbers in the detection number data (at each position on the incident surface 5a1) measured by the measurement device 7. The time point of the bottom is a time point of a bottom in time distribution of the detection numbers obtained in the condition that for each time point at and after the first time point, the detection number is expressed as a ratio to the above-described reference value. The data processing device 13 specifies a depth of a position of a cavity inside the inspection target 1 on the basis of the time point of the bottom and the second correspondence data stored in the storage device 12. The data processing device 13 outputs the specified depth. The output depth may be stored in an appropriate storage medium, may be displayed on a display, or may be printed on a sheet.

Fifth Example Based on Experiment

Figure 19A:
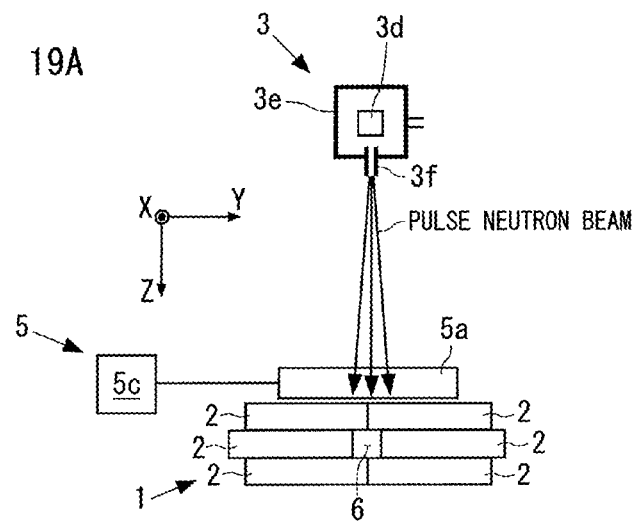
FIG. 19A illustrates a configuration of a fifth example based on experiment.
Figure 19B:
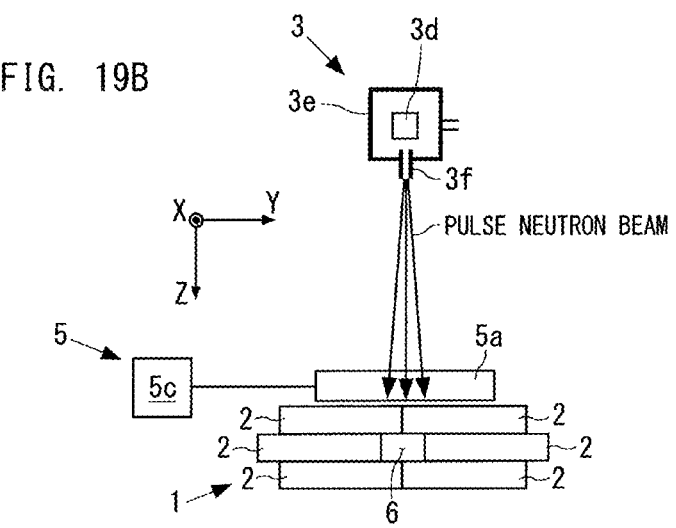
FIG. 19B illustrates another arrangement of the fifth example.
Figure 19C:
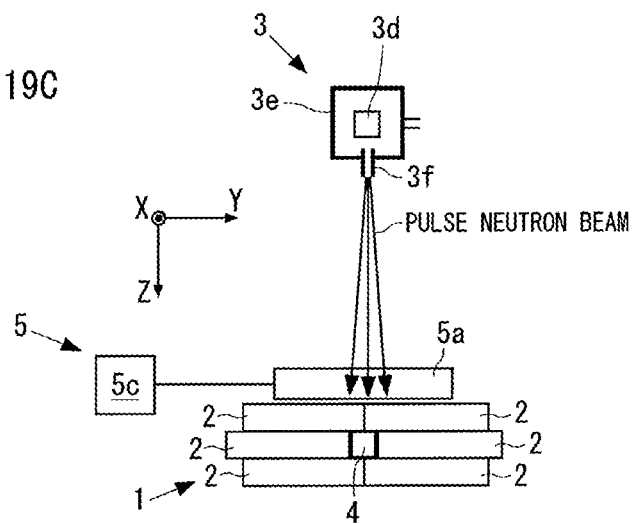
FIG. 19C illustrates still another arrangement of the fifth example.
Figure 19D:
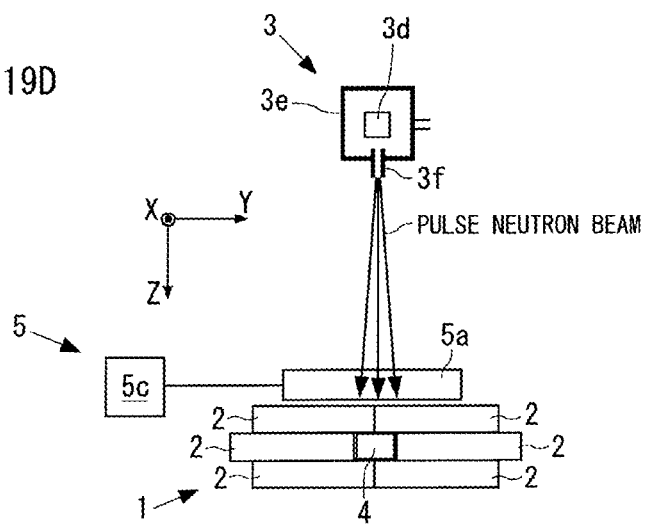
FIG. 19D illustrates still another arrangement of the fifth example.

FIGS. 19A to 19D illustrate a positional relation among the neutron source 3 of the non-destructive inspection device 10, the neutron detector 5a, and the inspection target 1 in a fifth example. In examples of FIGS. 19A to 19D, the neutron detection device 5 includes the above-described PSD 5a as the neutron detector 5a, and the position detection unit 5c. The inspection target 1 is a combination of a plurality of concrete blocks 2 that are rectangular parallelepipeds as illustrated in FIGS. 19A to 19D. The space 6 is formed inside the inspection target 1. The space 6 is configured as a cavity as illustrated in FIGS. 19A and 19B, or the acrylic block 4 that is a rectangular parallelepiped having substantially the same dimensions as those of the space 6 is disposed in the space 6 as illustrated in FIGS. 19C and 19D. A pulse neutron beam is made to be incident on the inspection target 1 from the neutron source 3 to measure the number of reflected neutrons detected in an area of a width of 100 mm from the center of the inspection target 1 in the y-axis direction.

In FIGS. 19A to 19D, the XYZ coordinate system is a coordinate system for representing dimensions of the inspection target 1. In FIGS. 19A to 19D, dimensions in the X-axis direction, the Y-axis direction, and the Z-axis direction of each of the concrete blocks 2 are 300 mm, 300 mm, and 60 mm, respectively.

In FIG. 19A, dimensions in the X-axis direction, the Y-axis direction, and the Z-axis direction of the space 6 are 300 mm, 50 mm, and 60 mm, respectively. In FIG. 19B, dimensions in the X-axis direction, the Y-axis direction, and the Z-axis direction of the space 6 are 300 mm, 100 mm, and 60 mm, respectively. In FIG. 19C, dimensions in the X-axis direction, the Y-axis direction, and the Z-axis direction of the acrylic block 4 are 300 mm, 50 mm, and 55 mm, respectively. In FIG. 19D, dimensions in the X-axis direction, the Y-axis direction, and the Z-axis direction of the acrylic block 4 are 300 mm, 100 mm, and 55 mm, respectively.

Figure 20:
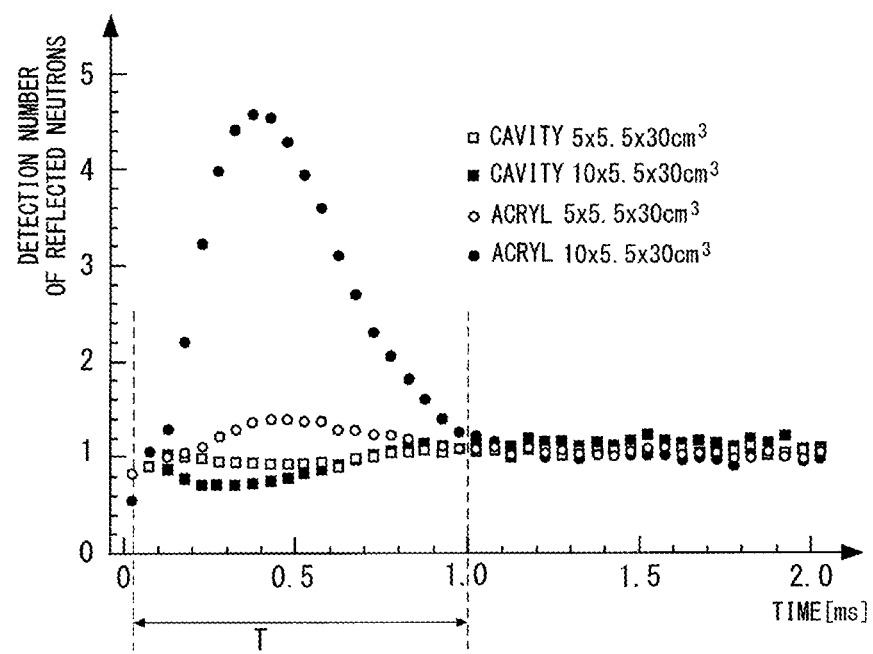
FIG. 20 illustrates measurement result in the fifth example.

FIG. 20 illustrates measurement results of the cases of FIGS. 19A to 19D. In FIG. 20, the horizontal axis represents a time with the origin being the above-described first time point, and the vertical axis represents the detection number detected by a specific photo detection element 5b2. The detection number represented by the vertical axis is normalized by setting, as a value of 1, the detection number in the case of FIG. 19A where the space 6 is filled with concrete. In FIG. 20, white squares, black squares, white circles, and black circles indicate the detection numbers in the cases of FIGS. 19A to 19D, respectively.

As understood from FIG. 20, when a volume of acryl increases by two times, the detection number increases by approximately 3.3 times at a peak time point.

An integrated value for detecting presence of acryl (water) and a cavity inside the inspection target 1 may be a value obtained by integrating the detection numbers over a time range T in which the detection number differs among the cases of FIGS. 19A to 19D. For example, the time range T may be a range from a time point of 0.03 milliseconds to a time point of 0.10 milliseconds in the horizontal axis of FIG. 20. However, the time range T is not limited thereto, and may be a range from a time point of 0.03 milliseconds to a time point of 0.15 milliseconds in another example.

The present invention is not limited to the above-described embodiment, and naturally, various modifications can be made without departing from the scope of the present invention. For example, any one of the following first to fifth additional embodiments may be adopted, or two or more of the first to fifth additional embodiments may be arbitrarily combined with each other to be adopted. In this case, respects that are not described below may be the same as those described above.

First Additional Embodiment

In the above description, the calculation device 9 may be omitted. In this case, the measurement device 7 outputs detection number data in which each time point of measurement at and after the first time point is associated with the detection number at the time point of measurement. The output detection number data may be stored in a storage device. The detection number data for each position on the incident surface 5a1 (e.g., each photo detection element 5b2) may be displayed on a display or printed on a sheet, directly from the measurement device 7 or through the above-described storage device. The detection number data changes depending on presence or absence of a defect inside the inspection target 1, and thus, a person can determine presence or absence of a defect inside the inspection target 1 by looking at the displayed or printed detection number data. In the first additional embodiment, the data processing device 11 described above may be omitted.

When the calculation device 9 is omitted, the above-described first correspondence data and second correspondence data can be created in advance. In this case, the measurement device 7 generates time distribution data that represent a time distribution of the detection numbers obtained by expressing the detection number (at each position on the incident surface 5a1) as a ratio to the above-described reference value for each time point at and after the first time point. The measurement device 7 outputs this time distribution data. The output time distribution data may be stored in a storage device. The time distribution data may be displayed on a display or printed on a sheet, directly from the measurement device 7 or through the storage device. Then, a person looks at the time distribution data generated by the measurement device 7 and displayed or printed, can specify a time point of a peak or a time point of a bottom of the detection numbers in time distribution data, and can compare the specified time point of the peak or the time point of the bottom with the first correspondence data or the second correspondence data to thereby obtain a depth of water or a cavity.

Second Additional Embodiment

Detection number data generated by the measurement device 7 may be an integrated value (total value) of detection numbers at and after the above-described second time point. In this case, the calculation device 9 described above is omitted. The integrated value for each photo detection element 5b2 that is generated by the measurement device 7 may be displayed or printed so as to be confirmed by a person, similarly to the above.

Third Additional Embodiment

In the configuration of FIG. 2A or 2B, the optical fiber 5b1 may be omitted, and each of the photo detection elements 5b2 may be directly attached to the scintillator 5a. In this case, the photo detection element 5b2 may be attached to each position on a surface on a side opposite to the incident surface 5a1 in the scintillator 5a.

Fourth Additional Embodiment

The neutron source 3 may be any kind of neutron source capable of radiating a pulse neutron beam to the inspection target 1. For example, in FIGS. 2A and 2B, the plurality of accelerators 3b1 and 3b2 are used, but a single accelerator may be used as long as energy of protons that is sufficient to generate neutrons is obtained.

A combination of accelerated particles, the energy of the particles, and the target 3d is not limited to the above-described contents as long as neutrons are generated with an amount thereof sufficient to inspect presence or absence of a defect of the inspection target 1.

Fifth Additional Embodiment

A configuration of the neutron detection device 5 is not limited to the above-described configuration as long as the measurement device 7 can generate detection number data on the basis of the detection of reflected neutrons that is performed by the neutron detection device 5. In other words, the neutron detection device 5 may be a device that uses the above-described scintillator or PSD as the neutron detector 5a, or may include another configuration. The neutron detector 5a of FIG. 11B may be a gas proportional counter having a configuration different from that in this drawing.

Also in the above-described first to fifth additional embodiments, the non-destructive inspection device 10 may include the above-described data processing device 11 that generates data expressing a plurality of integrated values in a two-dimensional coordinate area, as illustrated in FIG. 4.

The above-described matters may be described as follows.

(Supplementary Note 1)

A non-destructive inspection device including:

a neutron source that radiates a pulse neutron beam to a surface of an inspection target;

a neutron detection device that detects scattered neutrons that are scattered in the inspection target and returned; and a measurement device that measures the detection number of the scattered neutrons detected by the neutron detection device, and generates detection number data expressing the detection number with respect to time.

(Supplementary Note 2)

The non-destructive inspection device according to the supplementary note 1, wherein the detection number data is data in which each time point of the measurement is associated with the detection number at the time point of the measurement.

(Supplementary Note 3)

The non-destructive inspection device according to the supplementary note 1, wherein the detection number data is an integrated value of the detection numbers at and after a second time point that arrives by elapse of a set time from a first time point at which the neutron source radiates the pulse neutron beam to the inspection target.

(Supplementary Note 4)

The non-destructive inspection device according to the supplementary note 3, wherein the second time point is set such that among the scattered neutrons that are included in the pulse neutron beam radiated to the inspection target at the first time point, scattered in the inspection target, and returned, a predetermined proportion or more of the scattered neutrons that have energy greater than a set value occur during a period from the first time point to the second time point.

(Supplementary Note 5)

The non-destructive inspection device according to the supplementary note 3, wherein the second time point is set such that among the scattered neutrons that are included in the pulse neutron beam radiated to the inspection target at the first time point, scattered in the inspection target, and returned, a predetermined proportion or more of the scattered neutrons that have energy equal to or less than a set value occur at and after the second time point.

(Supplementary Note 6)

The non-destructive inspection device according to any one of the supplementary notes 1 to 5, wherein the neutron detection device detects scattered neutrons for each position on an incident surface facing the surface of the inspection target, and wherein the measurement device generates the detection number data for each position on the incident surface.

(Supplementary Note 7)

The non-destructive inspection device according to the supplementary note 6, wherein the neutron detection device includes a scintillator that is disposed at a position facing the surface of the inspection target, and the scintillator includes the incident surface on which the scattered neutrons from the surface are incident, and emits light by the incident scattered neutrons, i. wherein the neutron detection device includes a photo detector that detects light emission caused by the scattered neutrons incident at each position on the incident surface, ii. wherein the measurement device measures the number of times of the light emission detected by the photo detector as the detection number, and generates detection number data expressing the detection number with respect to time, and wherein the photo detector includes an optical fiber that is provided so as to correspond to each position on the incident surface, and a photo detection element that detects light emission caused by the scattered neutrons incident on each position on the incident surface, through the optical fiber corresponding to the position.

(Supplementary Note 8)

The non-destructive inspection device according to the supplementary note 6, wherein the neutron detection device includes a scintillator that is disposed at a position facing the surface of the inspection target, and the scintillator includes the incident surface on which the scattered neutrons from the surface are incident, and emits light by the incident scattered neutrons, wherein the neutron detection device includes a photo detector that detects light emission caused by the scattered neutrons incident at each position on the incident surface, wherein the measurement device measures the number of times of the light emission detected by the photo detector as the detection number, and generates detection number data expressing the detection number with respect to time, and wherein the scintillator is disposed away from a passage area of the pulse neutron beam directed to the inspection target from the neutron source, so as to be positioned in a vicinity of the passage area.

(Supplementary Note 9)

The non-destructive inspection device according to the supplementary note 2, further including:

a storage device that stores correspondence data in which a depth that is a length from a surface of the test object of a same material as that of the inspection target and that represents a position of water or a cavity inside the test object is associated with a time point of a peak or a time point of a bottom of the detection numbers; and a data processing device that specifies a time point of a peak or a time point of a bottom in the detection number data, and specifies a depth of water or a cavity inside the inspection target on the basis of the specified time point of the peak or time point of the bottom and the correspondence data, wherein the time point of the peak or the time point of the bottom in each of the correspondence data and the detection number data is a time point of a peak or a time point of a bottom in time distribution of the detection numbers obtained by expressing the detection number as a ratio to a reference value for each time point, and the reference value is determined for each time point, and is the detection number obtained at the time point for the test object in a standard state where neither water nor a cavity exists therein.

(Supplementary Note 10)

A non-destructive inspection method including:

making a pulse neutron beam incident on a surface of an inspection target, and detecting scattered neutrons that are scattered in the inspection target and returned; and measuring the detection number of the scattered neutrons, and generating detection number data expressing the detection number with respect to time.

REFERENCE SIGNS LIST

1: inspection target
1$a$: surface
2: concrete block
2$a$: incident surface
3: neutron source
3$a$: charged particle source
3$b$: acceleration device
3$b$1, 3$b$2: accelerator
3$c$: beam adjuster
3$d$: target
3$e$: container
3$f$: tubular shielding member
4: acrylic block
5: neutron detection device
5$a$: neutron detector (scintillator, PSD)
5$a$1: incident surface
5$b$: photo detector
5$b$1: optical fiber
5$b$2: photo detection element
6: space
7: measurement device
9: calculation device
10: non-destructive inspection device
11: data processing device
12: storage device
13: data processing device

The invention claimed is:

1. A non-destructive inspection method comprising:
making a pulse neutron beam incident on a surface of an inspection target;
detecting scattered neutrons that are scattered in the inspection target and returned;
measuring a detection number of the scattered neutrons at measurement time points wherein each detection number indicates a scalar amount;

generating detection number data expressing each detection number with respect to time wherein the detection number data is an integrated value of the detection numbers at and after a second time point that arrives by elapse of a set time from a first time point at which the neutron source radiates the pulse neutron beam to the inspection target; and detecting a state of the inspection target on the basis of the integrated value, wherein the second time point is set such that among the scattered neutrons that are included in the pulse neutron beam radiated to the inspection target at the first time point, scattered in the inspection target, and returned, a first predetermined proportion or more of the scattered neutrons that have energy equal to or less than a preset value occur at and after the second time point.

2. The non-destructive inspection method according to claim 1, wherein the second time point is set such that among the scattered neutrons that are included in the pulse neutron beam radiated to the inspection target at the first time point, scattered in the inspection target, and returned, a second predetermined proportion or more of the scattered neutrons that have energy greater than a preset value occur during a period from the first time point to the second time point.

3. The non-destructive inspection method according to claim 1, wherein the first predetermined proportion is a fixed proportion within a range from 10% to 98%.

4. The non-destructive inspection method according to claim 2, wherein the second predetermined proportion is a fixed proportion within a range from 50% to 100%.

5. The non-destructive inspection method according to claim 1, wherein the state of the inspection target is a state that a cavity exists in the inspection target, or a state that water exists in the inspection target.

6. The non-destructive inspection method according to claim 2, wherein the state of the inspection target is a state that a cavity exists in the inspection target, or a state that water exists in the inspection target.

7. The non-destructive inspection method according to claim 1, including:
determining that a cavity exists in the inspection target, when the integrated value is smaller than a standard value, or
determining that water exists in the inspection target, when the integrated value is larger than a standard value.

8. The non-destructive inspection method according to claim 1, including:
stopping radiation of the pulse neutron beam before the second time point.

9. The non-destructive inspection method according to claim 1, including:
setting the second time point by experiment or simulation.

10. The non-destructive inspection method according to claim 1, wherein the inspection target that is an infrastructure.

11. The non-destructive inspection method according to claim 10, wherein the infrastructure is a runway of an airport, a road of cars, a tunnel structure, or a bridge.

12. A non-destructive inspection device comprising:
a neutron source configured to radiate a pulse neutron beam to a surface of an inspection target;
a neutron detection device configured to detect scattered neutrons that are scattered in the inspection target and returned; and
a measurement device configured to measure a detection number of the scattered neutrons detected by the neutron detection device at measurement time points, and to generate detection number data expressing the detection number with respect to time wherein each detection number indicates a scalar amount,
wherein the detection number data is an integrated value of the detection numbers at and after a second time point that arrives by elapse of a set time from a first time point at which the neutron source radiates the pulse neutron beam to the inspection target,
the second time point is set such that among the scattered neutrons that are included in the pulse neutron beam radiated to the inspection target at the first time point, scattered in the inspection target, and returned, a first predetermined proportion or more of the scattered neutrons that have energy equal to or less than a preset value occur at and after the second time point.

13. The non-destructive inspection device according to claim 12, wherein the second time point is set such that among the scattered neutrons that are included in the pulse neutron beam radiated to the inspection target at the first time point, scattered in the inspection target, and returned, a second predetermined proportion or more of the scattered neutrons that have energy greater than a preset value occur during a period from the first time point to the second time point.

14. The non-destructive inspection device according to claim 12, wherein the first predetermined proportion is a fixed proportion within a range from 10% to 98%.

15. The non-destructive inspection device according to claim 13, wherein the second predetermined proportion is a fixed proportion within a range from 50% to 100%.

16. The non-destructive inspection device according to claim 12, comprising a data processing device configured to, when the integrated value is smaller than a standard value, determine that a cavity exists in the inspection target and output a signal indicating existence of the cavity, or when the integrated value is larger than a standard value, determine that water exists in the inspection target and output a signal indicating existence of the water.

17. The non-destructive inspection device according to claim 13, comprising a data processing device configured to, when the integrated value is smaller than a standard value, determine that a cavity exists in the inspection target and output a signal indicating existence of the cavity, or when the integrated value is larger than a standard value, determine that water exists in the inspection target and output a signal indicating existence of the water.

18. The non-destructive inspection device according to claim 12, wherein the second time point is set by experiment or simulation.

19. The non-destructive inspection device according to claim 12, wherein the inspection target that is an infrastructure.

20. The non-destructive inspection device according to claim 19, wherein the infrastructure is a runway of an airport, a road of cars, a tunnel structure, or a bridge.

* * * * *